United States Patent
Vaisvila et al.

(10) Patent No.: US 9,896,726 B2
(45) Date of Patent: Feb. 20, 2018

(54) METHODS AND COMPOSITIONS FOR DISCRIMINATION BETWEEN CYTOSINE AND MODIFICATIONS THEREOF, AND FOR METHYLOME ANALYSIS

(71) Applicant: New England Biolabs, Inc., Ipswich, MA (US)

(72) Inventors: Romualdas Vaisvila, Ipswich, MA (US); Heidi E. Johnson, Ipswich, MA (US); Saulius Vainauskas, Newburyport, MA (US); Theodore B. Davis, Boxford, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 14/806,048

(22) Filed: Jul. 22, 2015

(65) Prior Publication Data
US 2015/0322506 A1 Nov. 12, 2015

Related U.S. Application Data

(62) Division of application No. 13/827,885, filed on Mar. 14, 2013, now Pat. No. 9,121,061.

(60) Provisional application No. 61/611,295, filed on Mar. 15, 2012.

(51) Int. Cl.
*C12N 9/78* (2006.01)
*C12Q 1/68* (2006.01)
*C12N 9/02* (2006.01)
*C12N 9/12* (2006.01)

(52) U.S. Cl.
CPC ......... *C12Q 1/6869* (2013.01); *C12N 9/0071* (2013.01); *C12N 9/1252* (2013.01); *C12N 9/78* (2013.01); *C12Q 1/6827* (2013.01); *C12Y 114/11* (2013.01); *C12Y 207/07007* (2013.01); *C12Y 305/04005* (2013.01)

(58) Field of Classification Search
None
See application file for complete search history.

(56) References Cited

U.S. PATENT DOCUMENTS 6,368,801 B1 4/2002 Faruqi
2006/0210990 A1 9/2006 Todd et al.

FOREIGN PATENT DOCUMENTS

WO  WO2005005660  1/2005

OTHER PUBLICATIONS

GenBank Accession No. ADO85886.1, published Feb. 14, 2011.*
GenBank Accession No. ADO85890.1, published Feb. 14, 2011.*
GenBank Accession No. ADO85891.1, published Feb. 14, 2011.*
GenBank Accession No. AER45715.1, published Nov. 6, 2011.*
GenBank Accession No. AER45716.1, published Nov. 6, 2011.*
GenBank Accession No. AER45718.1, published Nov. 6, 2011.*

(Continued)

*Primary Examiner* — Richard C Ekstrom
(74) *Attorney, Agent, or Firm* — New England Biolabs, Inc.; Harriet M. Strimpel

(57) ABSTRACT

Compositions and methods are provided for discrimination between cytosine and modifications thereof using cytidine deaminases and/or oxygenases. Variants of wild type cytidine deaminases are described which show reduced bias with respect to adjacent nucleotides upstream of the cytosine. The methods provide a rapid and convenient use of enzymes to obtain methylomes.

15 Claims, 17 Drawing Sheets

(56) References Cited

OTHER PUBLICATIONS

GenBank Accession No. AER45719.1, published Nov. 6, 2011.*
GenBank Accession No. CAK54381.1, published Oct. 7, 2008.*
GenBank Accession No. XP_003264816.1, published May 6, 2011.*
GenBank Accession No. XP_001149270.2, published May 13, 2011.*
GenBank Accession No. XP_002667965.1, published Mar. 29, 2010.*
Frommer, et al., Proceedings of the National Academy of Sciences, 89.5:1827-1831 (1992).
Larijani, et al., Molecular Immunology, 42.5:599-604 (2005).
Booth, et al., Science, 336.6083:934-937 (2012).
Yu, et al., Cell, 149-1368-1380 (2012).
Kinney, et al., Journal of Biological Chemistry, 286, 28, 24685-24693, 2011.
ISA, Communication Relating to the Results of the Partial International Search, dated Jun. 19, 2013, International Application No. PCT/US2013/031620.

* cited by examiner

AC

A3A wt PURE extract

CC

A3A wt PURE extract

GC

A3A wt PURE extract

TC

A3A wt PURE extract

Human A3A   MEASPASGPRHLMDPHIFTSNFNNGRHKTYLCYEVERLDNGTSVKMDQHRGFLHNQAK   60
                                        V                M
Human A3A   NLLCGFYGRHAELRFLDLVPSLQLDPAQIYRVTWFISWSPCFSWGCAGEVRAFLQENTHV  120
                                                            Q
Human A3A   RLRIFAARIYDYDPLYKEALQMLRDAGAQVSIMTYDEFKHCWDTFVDHQGCPFQPWDGLD  180
              H                                                         E
Human A3A   EHSQALSGRLRAILQNQGN  199
            (SEQ ID NO:1)

```
Pan_troglodytes    MEASPASGPRHLMDPHIFTSNFTNGGRRKTYLCYEVERLDNGTLVKMDQHRGFLHNQAK    60
                                       N V    H                  M
Pan_troglodytes    NLLCGFYGQHAELRFLDLVPSLQLDPAQIYRVTWFISWSPCFSRGCAGQVRAFLQENTHV   120
                           R                                  M
Pan_troglodytes    RLRIFAARIYDYDPLYKEALQMLRDAGAQVSIMTYDEFKHCWDTFVDHQGCPFQPWDGLE   180
                     H
Pan_troglodytes    EHSQALSGRLRAILQNQGN    (SEQ ID NO:2)
                   199
```

*FIG. 5C*

```
AID wt      MDSLLMNRRKFLYQFKNVRWAKGRRETYLCYVVKRRDSATSFSLDFGYLRNKNGCHVELL     60
AID_E117Δ   MDSLLMNRRKFLYQFKNVRWAKGRRETYLCYVVKRRDSATSFSLDFGYLRNKNGCHVELL

AID wt      FLRYISDWDLDPGRCYRVTWFTSWSPCYDCARHVADFLRGNPNLSLRIFTARLYFCEDRK     120
AID_E117Δ   FLRYISDWDLDPGRCYRVTWFTSWSPCYDCARHVADFLRGNPNLSLRIFTARLYFC_DRK

AID wt      AEPEGLRRLHRAGVQIAIMTFKDYFYCWNTFVENHERTFKAWEGLHENSVRLSRQLRRIL    180
AID_E117Δ   AEPEGLRRLHRAGVQIAIMTFKDYFYCWNTFVENHERTFKAWEGLHENSVRLSRQLRRIL

AID wt      LPLYEVDDLRDAFRTLGL    (SEQ ID NO: 3)    198
AID_E117Δ   LPLYEVDDLRDAFRTLGL    (SEQ ID NO: 4)
```

FIG. 6A

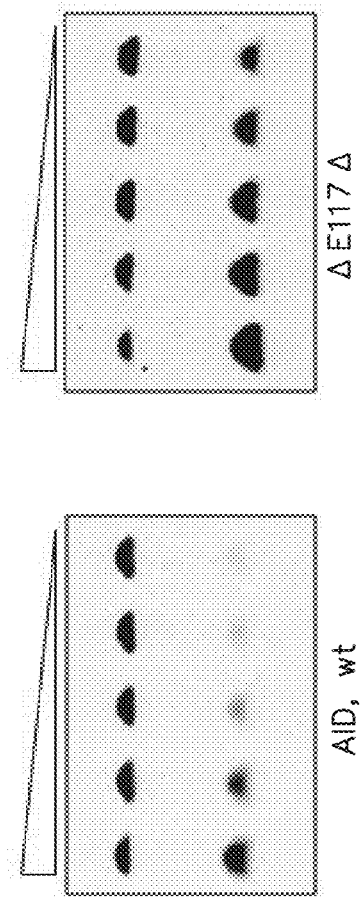

FIG. 6B 1) 2-Log DNA Ladder (NEB)
2) Control, no APOBEC3A
3-9) Serial 2x dilutions of APOBEC3A 5hm_C oligo  ATAAGAATAGAATGAAT5hmCTAAAAATGAATATGAATGAATAGTA/36-FAM/ (SEQ ID NO:5)

5hm_U oligo  ATAAGAATAGAATGAAT5hmUTAAAAATGAATATGAATGAATAGTA/36-FAM/ (SEQ ID NO:6)

SEQUENCE LISTING

<160> NUMBER OF SEQ ID NOS: 31

<210> SEQ ID NO 1
<211> LENGTH: 199
<212> TYPE: PRT
<213> ORGANISM: Homo sapiens

<400> SEQUENCE: 1

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

```
Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                    165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 2
<211> LENGTH: 199
<212> TYPE: PRT
<213> ORGANISM: Pan troglodytes

<400> SEQUENCE: 2

Met Glu Ala Ser Pro Ala Ser Gly Pro Arg His Leu Met Asp Pro His
1               5                   10                  15

Ile Phe Thr Ser Asn Phe Thr Asn Gly Ile Gly Arg Arg Lys Thr Tyr
                20                  25                  30

Leu Cys Tyr Glu Val Glu Arg Leu Asp Asn Gly Thr Leu Val Lys Met
            35                  40                  45

Asp Gln His Arg Gly Phe Leu His Asn Gln Ala Lys Asn Leu Leu Cys
        50                  55                  60

Gly Phe Tyr Gly Cys His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Arg Gly Cys Ala Gly Gln Val Arg Ala
                100                 105                 110

Phe Leu Gln Glu Asn Thr His Val Arg Leu Arg Ile Phe Ala Ala Arg
            115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                    165                 170                 175

Asp Gly Leu Asp Glu His Ser Gln Ala Leu Ser Gly Arg Leu Arg Ala
                180                 185                 190

Ile Leu Gln Asn Gln Gly Asn
        195

<210> SEQ ID NO 3
<211> LENGTH: 198
<212> TYPE: PRT
<213> ORGANISM: Homo sapiens

<400> SEQUENCE: 3

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
            35                  40                  45
```

```
Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
                115                 120                 125

Leu His Arg Ala Gly Val Gln Ile Ala Ile Met Thr Phe Lys Asp Tyr
                130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
                180                 185                 190

Phe Arg Thr Leu Gly Leu
                195

<210> SEQ ID NO 4
<211> LENGTH: 197
<212> TYPE: PRT
<213> ORGANISM: Homo sapiens

<400> SEQUENCE: 4

Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
                20                  25                  30

Val Lys Arg Arg Asp Ser Ala Thr Ser Phe Ser Leu Asp Phe Gly Tyr
                35                  40                  45

Leu Arg Asn Lys Asn Gly Cys His Val Glu Leu Leu Phe Leu Arg Tyr
        50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Asp Arg Lys Ala Glu Pro Glu Gly Leu Arg Arg Leu
                115                 120                 125

His Arg Ala Gly Val Gln Ile Ala Ile Met Thr Phe Lys Asp Tyr Phe
                130                 135                 140

Tyr Cys Trp Asn Thr Phe Val Glu Asn His Glu Arg Thr Phe Lys Ala
145                 150                 155                 160

Trp Glu Gly Leu His Glu Asn Ser Val Arg Leu Ser Arg Gln Leu Arg
                165                 170                 175

Arg Ile Leu Leu Pro Leu Tyr Glu Val Asp Asp Leu Arg Asp Ala Phe
                180                 185                 190

Arg Thr Leu Gly Leu
                195
```

```
<210> SEQ ID NO 5
<211> LENGTH: 44
<212> TYPE: DNA
<213> ORGANISM: Homo sapiens
<220> FEATURE:
<221> NAME/KEY: modified_base
<222> LOCATION: (18)..(18)
<223> OTHER INFORMATION: hydroxymethylated cytosine

<400> SEQUENCE: 5
ataagaatag aatgaatcta aaatgaata tgaaatgaat agta                44

<210> SEQ ID NO 6
<211> LENGTH: 44
<212> TYPE: DNA
<213> ORGANISM: Homo sapiens
<220> FEATURE:
<221> NAME/KEY: modified_base
<222> LOCATION: (18)..(18)
<223> OTHER INFORMATION: hydroxymethylated uracil

<400> SEQUENCE: 6
ataagaatag aatgaatuta aaatgaata tgaaatgaat agta                44

<210> SEQ ID NO 7
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (5)..(5)
<223> OTHER INFORMATION: methylated cytosine
<220> FEATURE:
<221> NAME/KEY: modified_base
<222> LOCATION: (12)..(12)
<223> OTHER INFORMATION: hydroxymethylated cytosine

<400> SEQUENCE: 7
gggtcggacc gc                                                  12

<210> SEQ ID NO 8
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (5)..(5)
<223> OTHER INFORMATION: methylated cytosine
<220> FEATURE:
<221> NAME/KEY: modified_base
<222> LOCATION: (12)..(12)
<223> OTHER INFORMATION: hydroxymethylated cytosine

<400> SEQUENCE: 8
gggtcggauu gc                                                  12

<210> SEQ ID NO 9
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (12)..(12)
<223> OTHER INFORMATION: hydroxymethylated cytosine
```

<400> SEQUENCE: 9
gggttggauu gc                                                         12

<210> SEQ ID NO 10
<211> LENGTH: 12
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (5)..(5)
<223> OTHER INFORMATION: 5-hydroxymethylcytosine or
      5-carboxymethylcytosine
<220> FEATURE:
<221> NAME/KEY: modified_base
<222> LOCATION: (12)..(12)
<223> OTHER INFORMATION: 5-hydroxymethylcytosine or
      5-carboxymethylcytosine

<400> SEQUENCE: 10
gggtcggauu gc                                                         12

<210> SEQ ID NO 11
<211> LENGTH: 12
<212> TYPE: DNA
<213> ORGANISM: Artificial Sequence
<220> FEATURE:
<223> OTHER INFORMATION: Synthetic construct

<400> SEQUENCE: 11
gggtcggatt gc                                                         12

<210> SEQ ID NO 12
<211> LENGTH: 12
<212> TYPE: DNA
<213> ORGANISM: Artificial Sequence
<220> FEATURE:
<223> OTHER INFORMATION: Synthetic construct

<400> SEQUENCE: 12
gggttggatt gc                                                         12

<210> SEQ ID NO 13
<211> LENGTH: 489
<212> TYPE: DNA
<213> ORGANISM: Artificial Sequence
<220> FEATURE:
<223> OTHER INFORMATION: Synthetic construct

<400> SEQUENCE: 13
gttaacgagg aggaaaagag aaatggagtg tgggatgagg aaaaggaaca gagaacctgt      60
ccccattgga gaccacaaca gaagccggca cagctttgtc cctgtttcct ttccctgaat     120
gactccagtt ccttctcagt gaagttggca gactgagcca ggtcccacag atctatcacc    180
cggggctctt caaactctgc aggagagcaa gggctgtcta taggtggcaa gtcaggacac    240
accaccggtg ctggggtcca agtgtcttgt catcccaagg gaatagtgtg ggttgcaact    300
tgggagcact aagtacctgg tctgtgctca cagctccagc ttagatgcag cttgattgaa    360
tccggctgca ccagtggagg gggtcacatg ctctagaccc agaatcaact gctacccctg    420
cccagggcca tcagcctgct cctggctctc aatcaaaagt gagtgagagg agaggtgtga    480
gaggatatc                                                            489

<210> SEQ ID NO 14
<211> LENGTH: 489
<212> TYPE: DNA
<213> ORGANISM: Artificial Sequence
<220> FEATURE:
<223> OTHER INFORMATION: Synthetic construct

<400> SEQUENCE: 14

| | | | | | |
|---|---|---|---|---|---|
| gttaaugagg | aggaaaagag | aaatggagtg | tgggatgagg | aaaaggaaua | gagaauutgt | 60 |
| uuuuattgga | gauuauaaua | gaagucggua | uagutttgtu | uutgtttuut | ttuuutgaat | 120 |
| gautuuagtt | uuttutuagt | gaaguuggua | gautgaguua | ggtuuuauag | atutatuauu | 180 |
| cggggututt | uaaautututgu | aggagaguaa | gggutgtuta | taggtgguaa | gtaaggauau | 240 |
| auuaucggtg | utggggtuua | agtgtuttgt | uatuuuaagg | gaatagtgtg | ggttguaaut | 300 |
| tgggaguaut | aagtauutgg | tutgtgutua | uagutuuagu | ttagatguag | uttgattgaa | 360 |
| tucggutgua | uuagtggagg | gggtuauatg | ututagauuu | agaatuaaut | gutauuuutg | 420 |
| uuuagggtuua | tuaguutgut | uutggututu | aatuaaaagt | gagtgagagg | agaggtgtga | 480 |
| gaggatatu | | | | | | 489 |

<210> SEQ ID NO 15
<211> LENGTH: 489
<212> TYPE: DNA
<213> ORGANISM: Artificial Sequence
<220> FEATURE:
<223> OTHER INFORMATION: Synthetic construct

<400> SEQUENCE: 15

| | | | | | |
|---|---|---|---|---|---|
| gttaaugagg | aggaaaagag | aaatggagtg | tgggatgagg | aaaaggaaua | gagaauutgt | 60 |
| uuuuattgga | gauuauaaua | gaagutggua | uagutttgtu | uutgtttuut | ttuuutgaat | 120 |
| gautuuagtt | uuttutuagt | gaaguuggua | gautgaguua | ggtuuuauag | atutatuauu | 180 |
| tggggututt | uaaautututgu | aggagaguaa | gggutgtuta | taggtgguaa | gtaaggauau | 240 |
| auuautggtg | utggggtuua | agtgtuttgt | uatuuuaagg | gaatagtgtg | ggttguaaut | 300 |
| tgggaguaut | aagtauutgg | tutgtgutua | uagutuuagu | ttagatguag | uttgattgaa | 360 |
| tutggutgua | uuagtggagg | gggtuauatg | ututagauuu | agaatuaaut | gutauuuutg | 420 |
| uuuagggtuua | tuaguutgut | uutggututu | aatuaaaagt | gagtgagagg | agaggtgtga | 480 |
| gaggatatu | | | | | | 489 |

<210> SEQ ID NO 16
<211> LENGTH: 489
<212> TYPE: DNA
<213> ORGANISM: Artificial Sequence
<220> FEATURE:
<223> OTHER INFORMATION: Synthetic construct

<400> SEQUENCE: 16

| | | | | | |
|---|---|---|---|---|---|
| gttaatgagg | aggaaaagag | aaatggagtg | tgggatgagg | aaaaggaata | gagaatttgt | 60 |
| ttttattgga | gattataata | gaagttggta | tagttttgtt | tttgtttttt | tttttgaat | 120 |
| gattttagtt | ttttttagt | gaagttggta | gattgagtta | ggttttatag | atttattatt | 180 |
| tggggttttt | taaattttgt | aggagagtaa | gggttgttta | taggtggtaa | gttaggatat | 240 |
| attattggtg | ttggggttta | agtgttttgt | tattttaagg | gaatagtgtg | ggttgtaatt | 300 |
| tgggagtatt | aagtatttgg | tttgtgttta | tagttttagt | ttagatgtag | tttgattgaa | 360 |
| tttggttgta | ttagtggagg | gggttatatg | ttttagattt | agaattaatt | gttattttg | 420 | tttagggtta ttagtttgtt tttggttttt aattaaaagt gagtgagagg agaggtgtga    480 gaggatatt                                                           489

<210> SEQ ID NO 17
<211> LENGTH: 71
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (38)..(38)
<223> OTHER INFORMATION: methylated cytosine

<400> SEQUENCE: 17
tatggggaag gttagggaag ataagaatag aatgatucta aggatgaata tgaggtgagg    60
agtaggatgg g                                                         71

<210> SEQ ID NO 18
<211> LENGTH: 49
<212> TYPE: DNA
<213> ORGANISM: Artificial Sequence
<220> FEATURE:
<223> OTHER INFORMATION: Primer

<400> SEQUENCE: 18
catctcatcc ctgcgtgtct ccgactcagt atggggaagg ttagggaag                49

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
cctctctatg ggcagtcggt gatcccatcc tactcctcac ctc                      43

<210> SEQ ID NO 20
<211> LENGTH: 26
<212> TYPE: DNA
<213> ORGANISM: Artificial Sequence
<220> FEATURE:
<223> OTHER INFORMATION: Primer

<400> SEQUENCE: 20
aggaggaaaa gagaaatgga gtgtgg                                         26

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ctcacacctc tcctctcact cac                                            23

<210> SEQ ID NO 22
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (31)..(31)
<223> OTHER INFORMATION: methylcytosine

<400> SEQUENCE: 22
cggcgtttcc gggttccata ggctccgccc cggactctga tgaccagggc atcaca     56

<210> SEQ ID NO 23
<211> LENGTH: 321
<212> TYPE: PRT
<213> ORGANISM: Naegleria gruberi

<400> SEQUENCE: 23

Met Thr Thr Phe Lys Gln Gln Thr Ile Lys Glu Lys Glu Thr Lys Arg
1               5                   10                  15

Lys Tyr Cys Ile Lys Gly Thr Thr Ala Asn Leu Thr Gln Thr His Pro
            20                  25                  30

Asn Gly Pro Val Cys Val Asn Arg Gly Glu Glu Val Ala Asn Thr Thr
        35                  40                  45

Thr Leu Leu Asp Ser Gly Gly Ile Asn Lys Lys Ser Leu Leu Gln
    50                  55                  60

Asn Leu Leu Ser Lys Cys Lys Thr Thr Phe Gln Gln Ser Phe Thr Asn
65                  70                  75                  80

Ala Asn Ile Thr Leu Lys Asp Glu Lys Trp Leu Lys Asn Val Arg Thr
                85                  90                  95

Ala Tyr Phe Val Cys Asp His Asp Gly Ser Val Glu Leu Ala Tyr Leu
            100                 105                 110

Pro Asn Val Leu Pro Lys Glu Leu Val Glu Phe Thr Glu Lys Phe
        115                 120                 125

Glu Ser Ile Gln Thr Gly Arg Lys Lys Asp Thr Gly Tyr Ser Gly Ile
130                 135                 140

Leu Asp Asn Ser Met Pro Phe Asn Tyr Val Thr Ala Asp Leu Ser Gln
145                 150                 155                 160

Glu Leu Gly Gln Tyr Leu Ser Glu Ile Val Asn Pro Gln Ile Asn Tyr
                165                 170                 175

Tyr Ile Ser Lys Leu Leu Thr Cys Val Ser Ser Arg Thr Ile Asn Tyr
            180                 185                 190

Leu Val Ser Leu Asn Asp Ser Tyr Tyr Ala Leu Asn Asn Cys Leu Tyr
        195                 200                 205

Pro Ser Thr Ala Phe Asn Ser Leu Lys Pro Ser Asn Asp Gly His Arg
    210                 215                 220

Ile Arg Lys Pro His Lys Asp Asn Leu Asp Ile Thr Pro Ser Ser Leu
225                 230                 235                 240

Phe Tyr Phe Gly Asn Phe Gln Asn Thr Glu Gly Tyr Leu Glu Leu Thr
                245                 250                 255

Asp Lys Asn Cys Lys Val Phe Val Gln Pro Gly Asp Val Leu Phe Phe
            260                 265                 270

Lys Gly Asn Glu Tyr Lys His Val Val Ala Asn Ile Thr Ser Gly Trp
        275                 280                 285

Arg Ile Gly Leu Val Tyr Phe Ala His Lys Gly Ser Lys Thr Lys Pro
    290                 295                 300

Tyr Tyr Glu Asp Thr Gln Lys Asn Ser Leu Lys Ile His Lys Glu Thr
305                 310                 315                 320

Lys

<210> SEQ ID NO 24

<211> LENGTH: 321
<212> TYPE: PRT
<213> ORGANISM: Naegleria gruberi

<400> SEQUENCE: 24

Met Thr Thr Phe Lys Gln Gln Thr Ile Lys Glu Lys Glu Thr Lys Arg
1               5                   10                  15

Lys Tyr Cys Ile Lys Gly Thr Ala Asn Leu Thr Gln Thr His Pro
            20                  25                  30

Asn Gly Pro Val Cys Val Asn Arg Gly Glu Val Ala Asn Thr Thr
        35                  40                  45

Thr Leu Leu Asp Ser Gly Gly Gly Ile Asn Lys Lys Ser Leu Leu Gln
    50                  55                  60

Asn Leu Leu Ser Lys Cys Lys Thr Thr Phe Gln Gln Ser Phe Thr Asn
65                  70                  75                  80

Ala Asn Ile Thr Leu Lys Asp Glu Lys Trp Leu Lys Asn Val Arg Thr
                85                  90                  95

Ala Tyr Phe Val Cys Asp His Asp Gly Ser Val Glu Leu Ala Tyr Leu
            100                 105                 110

Pro Asn Val Leu Pro Lys Glu Leu Val Glu Glu Phe Thr Glu Lys Phe
        115                 120                 125

Glu Ser Ile Gln Thr Gly Arg Lys Lys Asp Thr Gly Tyr Ser Gly Ile
    130                 135                 140

Leu Asp Asn Ser Met Pro Phe Asn Tyr Val Thr Ala Asp Leu Ser Gln
145                 150                 155                 160

Glu Leu Gly Gln Tyr Leu Ser Glu Ile Val Asn Pro Gln Ile Asn Tyr
                165                 170                 175

Tyr Ile Ser Lys Leu Leu Thr Cys Val Ser Ser Arg Thr Ile Asn Tyr
            180                 185                 190

Leu Val Ser Leu Asn Asp Ser Tyr Tyr Ala Leu Asn Asn Cys Leu Tyr
        195                 200                 205

Pro Ser Thr Ala Phe Asn Ser Leu Lys Pro Ser Asn Asp Gly His Arg
    210                 215                 220

Ile Arg Lys Pro His Lys Asp Asn Leu Asp Ile Thr Pro Ser Ser Leu
225                 230                 235                 240

Phe Tyr Phe Gly Asn Phe Gln Asn Thr Glu Gly Tyr Leu Glu Leu Thr
                245                 250                 255

Asp Lys Asn Cys Lys Val Phe Val Gln Pro Gly Asp Val Leu Phe Phe
            260                 265                 270

Lys Gly Asn Glu Tyr Lys His Val Val Ala Asn Ile Thr Ser Gly Trp
        275                 280                 285

Arg Ile Gly Leu Val Tyr Phe Ala His Lys Gly Ser Lys Thr Lys Pro
    290                 295                 300

Tyr Tyr Glu Asp Thr Gln Lys Asn Ser Leu Lys Ile His Lys Glu Thr
305                 310                 315                 320

Lys

<210> SEQ ID NO 25
<211> LENGTH: 174
<212> TYPE: PRT
<213> ORGANISM: Naegleria gruberi

<400> SEQUENCE: 25

Met Pro Met Asn Tyr Ile Thr Ser Asp Leu Lys Thr Gln Leu Gly Glu
1               5                   10                  15

-continued

```
Tyr Leu Ile Gly Ile Val Asn Pro Met Leu Asp Glu Thr Ile Thr Ala
            20                  25                  30
Ala Leu Glu Ile Leu Ser Pro Arg Thr Ile Asn Tyr Leu Thr Ser Leu
        35                  40                  45
Pro His Pro Tyr His Ile Leu Asn Asn Cys Ile Tyr Pro Ser Thr Ala
    50                  55                  60
Phe Asn Tyr Leu Glu Pro Gln Ile Glu Lys His Arg Ile Lys Asn Ala
65                  70                  75                  80
His Lys Asp Thr Arg Asp Ala Thr Pro Ser Val Leu Phe Tyr Leu Gly
                85                  90                  95
Asp Tyr Asp Glu Lys Glu Gly Tyr Leu Glu Phe Pro Glu Gln Asn Cys
            100                 105                 110
Lys Val Phe Val Lys Pro Gly Asp Leu Leu Leu Phe Lys Gly Asn Lys
        115                 120                 125
Tyr Lys His Gln Val Ala Pro Ile Thr Ser Gly Thr Arg Leu Gly Leu
    130                 135                 140
Val Tyr Phe Ala His Lys Ala Cys Lys Val Met Asp Phe Tyr Asp Asp
145                 150                 155                 160
Tyr Gln Lys Glu Ser Leu Asn Lys His Lys Gln Gln Asn Gln
                165                 170
```

<210> SEQ ID NO 26
<211> LENGTH: 583
<212> TYPE: PRT
<213> ORGANISM: Naegleria gruberi

<400> SEQUENCE: 26

```
Met Ser Ile Asn Thr Thr Phe Asn Gln Lys Thr Thr Gln Ser Gly Glu
1               5                   10                  15
Pro Pro Met Met Met Arg Met Thr Asn Ser Ser Thr Pro Pro Leu Thr
            20                  25                  30
Pro Lys Asn Cys Leu Pro Ile Phe Val Tyr Asn Asp Tyr Gly Lys Leu
        35                  40                  45
Ile Arg Glu Glu Gln Gln Pro Thr Asp Ile Ile Thr Asn Asn Asn
    50                  55                  60
Asn Ser Met Met Arg Ser Met Pro Thr Thr Asn Arg Trp Glu Thr Asn
65                  70                  75                  80
Pro Gln Thr Pro Leu Ser Val Ser Pro Phe Gln Pro Leu Leu Pro Ile
                85                  90                  95
Pro Asn Phe Ser His Ala Phe Ile Val Gly Asn Leu Pro Pro Ser Val
            100                 105                 110
Ser Val Arg Arg Lys Asn Arg Lys Met Ser Glu Lys Pro Lys Asn Asn
        115                 120                 125
Ser Ala Pro Ser Lys Ile Met His Gln Leu Glu Leu Ser Val Leu Asn
    130                 135                 140
Asn Gln Arg Arg Ile Ala Pro Lys Gly Pro Leu Ala Asp Ile Ser Asn
145                 150                 155                 160
Ile Gln Leu Pro Gln Gln Glu Ser Thr Asn Lys Ser Asn Asn Thr Thr
                165                 170                 175
Pro Lys Lys Pro Arg Ile Arg Gln Leu Met Leu Thr Thr Pro Leu Arg
            180                 185                 190
Glu Ser Leu Gln Ser Asn Gln Ser Ala Arg Ser Lys Tyr Ile Asp Glu
        195                 200                 205
Glu Ala Asn Asn Tyr Ser Ile Asn Asp Ser Pro Glu Thr Thr Ile Ile
    210                 215                 220
```

Lys Thr Ser Asn Thr Lys Asp Ser Glu His Lys Ala Met Ala Thr
225                 230                 235                 240

Asn Leu Gly Leu Ser Thr Asp Asp Phe Glu Cys Lys Pro Phe Glu Thr
            245                 250                 255

Thr Thr Leu Pro Ser Val Ile Asp Lys Asn Tyr Leu Val Val Asp Lys
        260                 265                 270

Glu Gly Cys Thr Gln Leu Ala Leu Leu Pro Asn His Ile Pro Thr Ser
    275                 280                 285

Val Cys Lys Leu Ile Glu Val Lys Cys Arg Lys Val Ser Asn Leu Arg
290                 295                 300

His Ala Leu Lys Ile Gln Lys Ala Ser Phe Tyr Val Asn Trp Trp Thr
305                 310                 315                 320

Lys Ser Gln Pro Met Gly Tyr Met Cys Lys Asp Asn Glu Ser Glu Ile
            325                 330                 335

Gly Lys Val Val Asn Glu Ile Ala Glu Leu Leu Ser Asp His Cys Arg
        340                 345                 350

Asn Leu Leu Arg Met Cys Asn Glu Arg Val Tyr Lys Lys Ile Ser Glu
    355                 360                 365

Leu Lys Glu Asp Lys Phe Phe Ala Pro Cys Ile Cys Phe Asn Ile Leu
370                 375                 380

Glu His Asp Leu Glu Ser Arg Ile Thr Lys Phe His His Asp Lys Met
385                 390                 395                 400

Asp Tyr Gly Val Ser Val Leu Phe Tyr Phe Gly Asp Tyr Ser Arg Gly
            405                 410                 415

Asn Leu Asn Val Leu Asp Ala Gly Ser Ser Thr Ile Val Thr Arg
        420                 425                 430

Pro Gly Asp Ala Val Ile Leu Arg Gly Asn Tyr Tyr Lys His Ser Val
    435                 440                 445

Gln Asn Ile Glu Pro Gly Asn Asn Lys Ala Arg Tyr Ser Ile Val Phe
450                 455                 460

Phe Ala His Ser Thr His Phe Leu Lys Lys Lys Tyr Glu Leu Ser Pro
465                 470                 475                 480

Ala Ala Ala Lys Lys Ala Phe Leu Val Asp Asn Pro Asp Phe Val Ser
            485                 490                 495

Ile Lys Lys Arg Lys Gln Ala Ser Ser Ser Asp Val Ser Val Lys
        500                 505                 510

Lys Ser Lys Lys Ser Thr Glu Asp Asn Val Glu Phe Ile Gln Thr His
    515                 520                 525

Thr Tyr Leu Gly Asn Gly Tyr Lys Ser Gly His Lys Asn Tyr Gln Tyr
530                 535                 540

Tyr Val Lys Phe Asn Asn Ser Asp Gln Lys Glu Trp Lys Ser Tyr Glu
545                 550                 555                 560

Ser Leu Pro Lys Gln Ala Val Ala Ser Tyr Trp Val Lys Phe Lys Lys
            565                 570                 575

Leu Lys Ser Leu Ser Asn Gln
        580

<210> SEQ ID NO 27
<211> LENGTH: 207
<212> TYPE: PRT
<213> ORGANISM: Naegleria gruberi

<400> SEQUENCE: 27

Met Leu Glu Ala Gln His His Lys Leu Thr Ile Tyr Thr Gly Met Trp

```
                1               5                   10                  15
            Gly His Met Lys Pro Cys Val Phe Ile Ala Ala Asp Asn Cys Asn Lys
                            20                  25                  30

Ser Gly Glu Thr Ile Val Glu Asn Leu Leu Phe Lys Leu Gly Lys Ile
                            35                  40                  45

Gly Ser Lys Leu Met Glu Ile Leu Ser Pro Phe Thr Met Asn Phe Leu
                50                      55                  60

Ser Ser Leu Asp Pro Glu Ile Phe Leu Asn His Asp Leu Phe Pro Ile
            65                      70                  75                  80

Ser Ala Thr Asn Phe Met Ile Pro Gly Asn Lys His Arg Ile Leu Lys
                            85                  90                      95

Pro His Lys Asp Asn Gln Asp Val Gly Leu Cys Ile Ile Phe Tyr Phe
                            100                 105                 110

Gly Asn Tyr Asn Ala Pro Leu Glu Phe Val Asn Lys Gly Ser Val Phe
                            115                 120                 125

Asn Thr Glu Arg Gly Asp Val Leu Leu Met Arg Gly Ser His Phe Arg
            130                     135                 140

His Val Val Lys Pro Val Asp Asn Gly Leu Leu Glu His Val His Asp
            145                     150                 155                 160

Pro Met Arg Ile Ser Val Val Leu Phe Ala His Lys Ser Leu Lys Met
                            165                 170                 175

Asn Pro Ser Tyr Phe Leu Asn Ala Gly Ser Ala Leu Lys Ala His Asp
                            180                 185                 190

Glu Asp Phe Pro Glu Lys Ala Lys Lys Arg Lys Lys Lys Arg Lys
                            195                 200                 205

<210> SEQ ID NO 28
            <211> LENGTH: 211
            <212> TYPE: PRT
            <213> ORGANISM: Naegleria gruberi

<400> SEQUENCE: 28

Met Phe Leu Arg Asn Ile Leu Pro Glu Asn Thr Thr Thr Glu Val Thr
            1               5                   10                  15

Asn Ile Leu Asp Lys Ile Asn Gln Arg Arg Ser Lys Glu Asn Tyr Tyr
                            20                  25                  30

Ile Gly Ser Trp Gly Lys Ser Ser Phe Leu Phe Lys Thr Asn Asp
                            35                  40                  45

Thr Ile Phe Asn Glu Leu Ser Ser Gln Phe Ile Lys Ile Asn Leu
                50                      55                  60

Leu Lys Asn Tyr Val Leu Glu Ile Leu Lys Phe Gly Asn Asn Lys Met
            65                      70                  75                  80

Arg Lys Phe Leu Glu Lys Tyr Asn Ser Ser Asp Phe Leu Ser Ile Tyr
                            85                  90                      95

Pro Thr Val Cys Phe Asn Phe Leu Asp Lys Ser Val Asp Glu Asn Arg
                            100                 105                 110

Ile Leu His Ile His Pro Asp Lys Glu Asp Thr Gly Thr Ser Leu Ile
                            115                 120                 125

Phe Tyr Phe Gly Lys Phe Lys Gly Gly Ala Ile Ser Phe Pro Glu Leu
                            130                 135                 140

Asn Phe Lys Leu Met Val Gln Ser Ala Asp Val Leu Leu Phe Asp Gly
            145                     150                 155                 160

Lys Asn Asn Leu His Ala Val Glu Ser Leu His Gly Lys Asp Asp Val
                            165                 170                 175
```

```
Arg Tyr Ser Val Val Phe Phe Ala His Lys Ala Asp Leu Gly Lys Thr
            180                 185                 190

Ser Tyr Pro Met Asn Arg Gly Glu Val Met Lys Gly Ile Lys Asn Lys
        195                 200                 205

Ile Asn Asn
    210

<210> SEQ ID NO 29
<211> LENGTH: 302
<212> TYPE: PRT
<213> ORGANISM: Naegleria gruberi

<400> SEQUENCE: 29

Met Asp Ile Gly Ile Asp Trp Arg Gly Thr His Phe Arg His Lys Asn
1               5                   10                  15

His Leu Val Lys Glu Val Cys Asp Arg Thr Asn Trp Ile Val Leu
            20                  25                  30

Cys Pro Asn Gly Gln Val Asp Ile Ala Phe Phe Pro Asn Ala Ile Pro
            35                  40                  45

Glu Glu Leu Cys Leu Glu Met Glu Thr Val Val Ala Asn Ser Asp Val
    50                  55                  60

Asp Ile Leu Ser Cys Lys Lys Ala Ile Ile Asp Gly Ser Trp Thr Arg
65                  70                  75                  80

Tyr Gly Asn Gly Ile Tyr Pro Val Lys Thr Ile Thr Thr Asn Gln Ser
                85                  90                  95

Ile Leu Leu His Glu Leu Asn Asp Lys Cys Gly Pro Phe Val Leu Asp
            100                 105                 110

Lys Leu Lys His Ile Asn Lys Asn Met Phe Asn Lys Leu Asp Asn Ile
        115                 120                 125

Asn Glu Asp Ile Lys Asn Tyr Lys Ile Phe Ala Lys Tyr Pro Thr Leu
    130                 135                 140

Ala Leu Asn Val Ser His Asn Glu Asn Tyr Asn Ile Ser Lys Lys Pro
145                 150                 155                 160

Tyr Arg Lys His Thr Asp Gly Asn Asp Ile Gly Leu Gly Val Leu Thr
                165                 170                 175

Tyr Phe Gly Ser Glu Ile Ile Glu Gly Gly Asn Leu Ile Ile His Ile
            180                 185                 190

Glu Asn Leu Lys Val Phe Asn Phe Pro Ile Gln Arg Arg Asp Leu Val
        195                 200                 205

Phe Leu Asn Ser Lys Phe Tyr Ala His Gln Val Thr Lys Val Thr Ser
    210                 215                 220

Gly Ile Arg Phe Gly Leu Val Tyr Phe Ala Gly Glu Ala His Phe Arg
225                 230                 235                 240

Val Arg Asn Asn Asp Asp Phe Leu Pro Ala Leu Pro Phe Asn Ala Asn
                245                 250                 255

Asp Lys Glu Leu Arg Glu Glu Arg Ser Lys Lys Gly Arg Lys Ser Met
            260                 265                 270

Asn Glu Tyr Lys Lys Arg Phe Leu Lys Lys Tyr Leu Arg Glu Lys Lys
        275                 280                 285

Lys Ile Asn Lys Lys Arg Val Lys Cys Lys Asn Lys Leu Lys
    290                 295                 300

<210> SEQ ID NO 30
<211> LENGTH: 575
<212> TYPE: PRT
<213> ORGANISM: Naegleria gruberi
```

<400> SEQUENCE: 30

```
Met Gly Pro Leu His Val Ser Gln His Asp Lys Lys Pro Lys His
1               5                   10                  15

Arg Arg Arg Lys Lys Gln Phe Leu Lys Ala Gln Ala Leu Thr Arg Val
                20                  25                  30

Cys Trp Glu Asn Glu Lys Ser Ile Asp Glu Ser Gly Lys Thr Arg Val
            35                  40                  45

Tyr Lys Met Ile Lys Glu Trp Glu Phe Leu Lys Gly Asn Asn Ile Gln
        50                  55                  60

Ser Asn Glu Pro Ile Leu Ser Val Tyr Gly Val Asn Asp Thr Ile Pro
65                  70                  75                  80

Lys Glu Ile Ser Ser Asn Thr Ile Ile Val Thr Lys Glu Gly Met Val
                85                  90                  95

Glu Met Ala Leu Leu Lys Ser Val Leu Pro Pro Ser Leu Leu Glu Glu
            100                 105                 110

Cys Thr Gln Leu Cys Arg Glu Met Ser Glu Trp Leu Ala Thr Glu Lys
        115                 120                 125

Asp Ile Asp Lys Gly Ser Phe Phe Ser Gly Trp Trp Thr Met Asn Met
130                 135                 140

Pro Met Gly Tyr Lys Cys Ala Asp Ser Phe Arg Phe Glu Leu Val Asp
145                 150                 155                 160

Thr Lys Val Lys Gln Ile Gln Ala Leu Leu His Asp Thr Phe Gln His
                165                 170                 175

Ile Leu Glu Leu Ala Asn Pro Lys Leu Phe Ala Lys Leu Ser Lys Leu
            180                 185                 190

Thr Glu Arg Gly Gln Thr Pro Val Val Cys Phe Asn Met Ile Pro Thr
        195                 200                 205

Arg Asn Glu Ser Val Lys Glu Lys Phe Gln Gly Ser Tyr Lys Ser Thr
210                 215                 220

Asp Lys Val Asn Arg Pro Lys Thr Asn His Arg Asp Arg Asn Asp Met
225                 230                 235                 240

Gly Ile Ser Ala Met Phe Tyr Met Gly Lys Phe Gly Gly Ser Leu
                245                 250                 255

Gln Leu Ile Arg Val Asn Glu His Thr Pro Lys Thr Leu Val His Ile
        260                 265                 270

Gln Ala Gly Asp Val Val Leu Leu Arg Ala Asn Lys Tyr Arg His Ala
            275                 280                 285

Val Ser Pro Thr Arg Pro Gln Ser Phe Pro Leu Ala Asn Ser Ser Gln
        290                 295                 300

Thr Glu Val Asp Asp Val Lys Ile Cys Glu Asn Ser Ser Pro Thr Leu
305                 310                 315                 320

Asn Asn Pro Gln Ala Asp Asp Asn Thr Pro Thr Leu Ile Asn Thr Cys
                325                 330                 335

Pro Lys Gln Glu Pro Thr Asp Gly Asp Asn Pro Val Gln Ser Ser Lys
            340                 345                 350

Glu Pro Ser Asn Asp Tyr Glu Gln Lys Arg Phe Ser Phe Ile Phe Phe
        355                 360                 365

Ala His Arg Ser His Phe Lys His Ser Lys Val Tyr Cys Gly Met Gly
        370                 375                 380

Gln Arg Gln Ala Leu Asn Ala Phe Lys Ala Asp His Pro Tyr Tyr Gln
385                 390                 395                 400

Ser Gln Arg Met Lys Lys Lys Leu Gly Asp Asp Cys Leu Asp Gln Ser
```

```
                    405                 410                 415
Leu Ile Leu Thr Glu Lys Arg Lys Pro Ile Lys Arg Asn Tyr Ala Leu
            420                 425                 430

Phe Asn Glu Cys Gly Asp Asp Lys Gln Glu Ser Asp Glu Glu Glu
            435                 440                 445

Tyr Gln Gln Tyr Glu Pro Lys Pro Thr Thr Glu Glu Tyr Thr Ile Lys
            450                 455                 460

Val Ile Val Asp His Glu Lys Val Phe Lys Gly Ser Asp Gln Ser Arg
465                 470                 475                 480

Lys Ser Tyr Leu Tyr His Ile Gln Trp Leu Gly Tyr Pro Asp Glu Thr
            485                 490                 495

Trp Glu Pro Tyr Glu His Leu Asp Asp Cys Gln Val Phe Glu Asp Tyr
            500                 505                 510

Leu Lys His His Asn Ile Ser Leu Phe Asp Glu Glu Glu Asp Arg
            515                 520                 525

Lys Val Asp Asp Ser Met Leu Leu Pro Ala Trp Met His Glu Asp Glu
            530                 535                 540

Ser Leu Phe Glu Ala Leu Leu Pro Ile Ile Cys Cys Ser Thr Asp Asn
545                 550                 555                 560

Pro Arg His His Leu Asp Asp Val Pro Pro Phe Asp Phe Asn Tyr
            565                 570                 575

<210> SEQ ID NO 31
<211> LENGTH: 253
<212> TYPE: PRT
<213> ORGANISM: Naegleria gruberi

<400> SEQUENCE: 31

Met Thr Glu Ile Val Glu Leu Ser Asn Ile Glu Pro Lys Asp Gln Lys
1               5                   10                  15

Gln Ala Ile Ile Gly Gly Thr Trp Asn Arg Tyr Gly Asn Ser Ile Glu
            20                  25                  30

Ile Val Ala Gly Ile Ser Asp Glu Asn Asn Thr Leu Leu Asp Asn Leu
            35                  40                  45

Thr Asn Cys Cys Glu Ser Phe Val Leu Asp Lys Leu Trp His Leu Asn
        50                  55                  60

Arg Ser Met Tyr Asn Lys Leu Asp Thr Ile Glu Glu Lys Ile Lys Asn
65              70                  75                  80

Phe Lys Thr Tyr Ala Lys Tyr Pro Ser Leu Ala Leu Asn Leu Leu Cys
            85                  90                  95

Lys Glu Asn Tyr Asn Gly Lys Val Lys Pro Tyr Arg Lys His Ile Asp
            100                 105                 110

Pro Asn Asn Asn Gly Met Asp Val Leu Met Phe Phe Gly Lys Thr Phe
            115                 120                 125

Glu Gly Gly Asn Leu Ile Val Ser Tyr His Tyr Thr Asn Ile Asp Phe
            130                 135                 140

Arg Met Phe Thr Leu Pro Ile Gln Ser Gly Asp Leu Val Phe Leu Asn
145                 150                 155                 160

Ser Arg Ile Tyr His His Lys Val Thr Lys Val Thr Ser Gly Val Arg
            165                 170                 175

Cys Gly Leu Val Phe Phe Ala Gly Leu Asp His Phe Ser Val Arg Lys
            180                 185                 190

Ala Asn Tyr Lys Lys Val Lys Lys Glu Glu Tyr Gln Lys Asn Met Asp
            195                 200                 205
```

```
Asp Lys Leu Leu Ala Leu Pro Phe Gln Gln Lys Asp Lys Asp Leu Arg
    210                 215                 220

Ile Glu Arg Thr Lys Thr Gly Arg Lys Glu Ile Lys Gln Phe His Lys
225                 230                 235                 240

Asn Leu Gln Asn Asn Leu Pro Asn Lys Lys Arg Lys Lys
                245                 250
```

METHODS AND COMPOSITIONS FOR DISCRIMINATION BETWEEN CYTOSINE AND MODIFICATIONS THEREOF, AND FOR METHYLOME ANALYSIS

REFERENCE TO RELATED APPLICATIONS

This application is a continuation of U.S. application Ser. No. 13/827,885 filed Mar. 14, 2013 which claims priority to U.S. Application No. 61/611,295 filed Mar. 15, 2012. The entire disclosure of each of the following patent applications is hereby incorporated by reference into the present application: U.S. Application No. 61/611,295, filed Mar. 15, 2012; U.S. Application No. 61/722,968, filed Nov. 6, 2012; U.S. Application No. 61/723,427, filed Nov. 7, 2012; U.S. Application No. 61/724,041, filed Nov. 8, 2012; U.S. application Ser. No. 13/804,804, filed Mar. 14, 2013; U.S. application Ser. No. 13/826,395, filed Mar. 14, 2013; and U.S. application Ser. No. 13/827,087, filed Mar. 14, 2013.

BACKGROUND

Cytidine deaminases include activation induced cytidine deaminase (AID) and apolipoprotein B mRNA editing enzymes, catalytic polypeptide-like (APOBEC). These enzymes are DNA mutators capable of inserting mutations into DNA and RNA by deaminating cytidine to form uridine. These enzymes play a role in antigen-driven antibody diversification processes and in an innate defense system against retroviruses. The human APOBEC family consists of 11 members: APOBEC-1 (Apo1), APOBEC-2 (Apo2), AID, APOBEC-3A, -3B, -3C, -3DE, -3F, -3G, -3H and APOBEC-4 (Apo4). Members of the APOBEC-3A family contain either single (A3A, A3C, A3H) or double (A3B, A3DE, A3F, and A3G) zinc-dependent deaminase domain (ZDD).

Attempts have been made to replace sodium bisulfite methylome sequencing (Frommer, et al., *Proceedings of the National Academy of Sciences*, 89.5:1827-1831 (1992)) by using AID (Larijani, et al., *Molecular Immunology*, 42.5: 599-604 (2005)). However problems were identified with the use of native AID including: difficulties in obtaining purified active enzyme due to toxicity in non-natural host cells, incomplete conversion of cytosine to uracil arising from low activity of enzymes and substrate bias, and a lack of in vitro assays suitable for selecting AID suitable for methylome sequencing. Hence, methylome sequencing continues to be performed by sodium bisulfite sequencing despite problems associated with this method that include the use of multiple biochemical steps, an inability to distinguish methyl from hydroxymethylcytosine, the requirement for heat to denature the DNA, additional shearing of DNA into small fragments by the chemical treatment, and a limitation on the length of a DNA that can be sequenced.

SUMMARY

In general, in one aspect, a protein variant, for example, a variant of a native cytidine deaminase is provided that includes a protein having at least 90% sequence homology or identity to APOBEC-3A and has at least one mutation. In an embodiment, a protein is provided having at least 90% sequence homology or identity to: (a) SEQ ID NO:1 and comprising at least one mutation at a position corresponding to an amino acid position selected from the group consisting of 25, 45, 109, 123 and 180 of SEQ ID NO:1; or (b) SEQ ID NO:2 and comprising at least one mutation at an amino position corresponding to 23, 25, 29, 45, 69, 104 or 123 of SEQ ID NO:2 or (c) SEQ ID NO:3 (AID) and having at least one mutation corresponding to a deletion at 117 of SEQ ID NO:4.

Embodiments include combining with the protein variant at least one of a purified oxygenase, a polymerase, a polynucleotide and/or at least one primer and dNTPs.

In general, in another aspect, an in vitro mixture is provided that includes a cytidine deaminase and a purified oxygenase.

Embodiments of the mixture may include one or more of the following features: the cytidine deaminase may include AID or mutant thereof; APOBEC or a mutant thereof; APOBEC-3A or a mutant thereof; or the compositions described above; and/or the oxygenase may be a methylpyrimidine oxygenase, for example, mYOX (eg mYOX1) or TET (eg TET1 or TET2 or TET3), a DNA polymerase; and/or at least one primer and dNTPs.

In general in one aspect, an in vitro mixture is provided that includes a cytidine deaminase and a DNA polymerase. The in vitro mixture may further include a polynucleotide and at least one primer and dNTPs.

In general, in one aspect, a method is provided for determining, for a cytidine deaminase, a cytosine preference according to an adjacent nucleotide, which includes: (a) reacting a polynucleotide (optionally single-stranded) containing a cytosine with a cytidine deaminase to convert the cytosine to uracil where the cytosine may be adjacent to any of adenine (A), guanine (G), thymine (T), uracil (U) or cytosine (C); (b) reacting the product of (a) with a glycosylase and an AP endonuclease so as to cleave the polynucleotide at the uracil; and (c) detecting the cleavage product from (b) to determine how the activity of the cytidine deaminase for the cytosine adjacent to any of A, G, T, U or C.

An embodiment may include one or more features for example, the cytidine deaminase may include AID or mutant thereof, APOBEC or a mutant thereof, APOBEC-3A or a mutant thereof or the compositions described above, and/or the polynucleotide may be single-stranded and may be labeled at one end.

In general in one aspect, a method for differentiating an unmethylated cytosine (C) or a 5-methylcytosine (5-mC) from a 5-hydroxymethylcytosine (5-hmC), 5-formylcytosine (5-fC), 5-carboxycytosine (5-CaC) or 5-glycosylated hmC (5-ghmC) that includes reacting a polynucleotide optionally containing C, 5-mC, 5-hmC, 5-fC, 5-CaC and/or 5-ghmC, with a cytidine deaminase wherein the 5-mC is converted to a T and only the C is converted to a U; and (b) amplifying or cleaving the polynucleotide to identify the location of at least one converted nucleotide in the polynucleotide.

For aspects of the invention described herein, the cytidine deaminase may be a protein variant as described above; the polynucleotide may be single-stranded, the oxygenase maybe a methylpyrimidine oxygenase such as mYOX1 or a 5-mC oxygenase such as TET1, TET2 and TET3, for example, TET1.

In an embodiment of the method, 5-mC may be differentiated from C, by additionally reacting the polynucleotide prior to (a) with an oxygenase so as to generate a sequence wherein only C is altered to uracil (U).

A further embodiment includes sequencing the polynucleotide in which C is converted to U only and sequencing the polynucleotide obtained in (a) where C is converted to U and 5-mC is converted to T and comparing the sequences to characterize 5-mC in the polynucleotide or alternatively, comparing the sequence of the deaminated polynucleotide from (a) with the sequence of the untreated polynucleotide.

Additional steps may include sequencing a first sample of the polynucleotide after the reaction with the oxygenase and cytidine deaminase to generate a first sequence; sequencing a second sample of the polynucleotide after a reaction with cytidine deaminase but not with the oxygenase to generate a second sequence; and optionally sequencing a third sample of the polynucleotide absent a reaction with the cytidine deaminase or the oxygenase; and comparing the first and at least one of the second and third sample sequences to detect cytosine and 5-mC or comparing the second sample sequence with at least one of the first and third sample sequences.

In another embodiment, cleaving the polynucleotide further includes cleaving the polynucleotide with a glycosylase and endonuclease at a U or cleaving the polynucleotide after DNA amplification, with a restriction endonuclease that recognizes a site after conversion of C to T in the polynucleotide.

Because mYOX1 acts as an oxygenase on single-stranded polynucleotide substrates, cytidine deaminases which also act on single-stranded polynucleotides can be added after the oxygenase reaction without the need to manipulate the substrate and optionally without changing the buffer or reaction vessel. It may be desirable to form the in vitro mixture described above during a polynucleotide analysis for the presence of 5-mC or it may be desirable to form an in vitro mixture of the oxygenase and cytidine deaminase prior to the reaction where the conditions are modulated so that the oxygenase acts on the polynucleotide substrate before the cytidine deaminase acts.

In an embodiment of the method, cytidine deaminase having the characteristics of the protein described above is added to the reaction mixture containing the oxygenase after completion of the oxidation reaction.

In general in one aspect, a method for differentiating a methyl 5-mC from a C is described that includes: reacting a first polynucleotide with sodium bisulfite reaction reagents followed by a cytidine deaminase in the absence of an oxygenase, thereby converting 5-mC to T and converting C to U; and reacting a second polynucleotide, comprising an identical nucleotide sequence, with sodium bisulfite sequencing reagents without subsequent exposure to a cytidine deaminase, thereby converting C to U only.

An embodiment may include amplifying or cleaving the first and second polynucleotides to identify the location of at least one converted nucleotide in the polynucleotides.

An embodiment may include one or of the following features: the cytidine deaminase is APOBEC-3A or variant thereof; the cytidine deaminase is a protein having at least 90% sequence homology with (a) SEQ ID NO:1 and comprising at least one mutation at a position corresponding to an amino acid position selected from the group consisting of 25, 45 109, 123 and 180 of SEQ ID NO:1; (b) SEQ ID NO:2 and comprising at least one mutation at an amino position corresponding to 23, 25, 29, 45, 69, 104 or 123 of SEQ ID NO:2 or (c) SEQ ID NO:3 (AID) and having at least one mutation corresponding to a deletion at 117 of SEQ ID NO:4; the 5-methylcytosine oxygenase is TET1, TET2 or TET3; the methylpyrimidine oxygenase is mYOX1 and/or the polynucleotide has a length of greater than 1 Kb.

An embodiment may include one or more of the following features: adding the cytidine deaminase to the reaction mixture containing the oxygenase after completion of the oxidation reaction; and/or performing the method at a temperature less than 60° C.

The embodiments described above may be used to construct a methylome map.

Lane 1: Protein ladder (New England Biolabs, Ipswich, Mass.) arrow approximates to a 25 kd band on the gel.

Lanes 2-7: Human APOBEC-3A was subcloned under a T7 phage promoter (2 clones, A3A-1 and A3A-2) and expressed in T7 Express Competent *E. coli* (New England Biolabs, Ipswich, Mass.). U=uninduced, T=after induction with 0.5 mM IPTG and cultivating 3 hours at 30° C., S=soluble fraction after induction with 0.5 mM IPTG and cultivating 3 hours at 30° C. No distinct bands corresponding to APOBEC-3A were observed.

Lanes 8-9: The same clones (A3A-1 and A3A-2) were expressed using PURExpress; the black arrow points to APOBEC-3A protein.

Lane 10 contains a control sample with no plasmid (A3A-1 or A3A-2) added in PURExpress. No band corresponding to AID or APOBEC-3A was observed.

Lane 11: A gene for human AID was subcloned under a T7 phage promoter, and expressed using PURExpress producing a band having a slightly larger molecular weight compared to APOBEC-3A than expected FIG. 2A-F shows an assay for determining the conversion of C to U using APOBEC-3A.

Figure 2A:
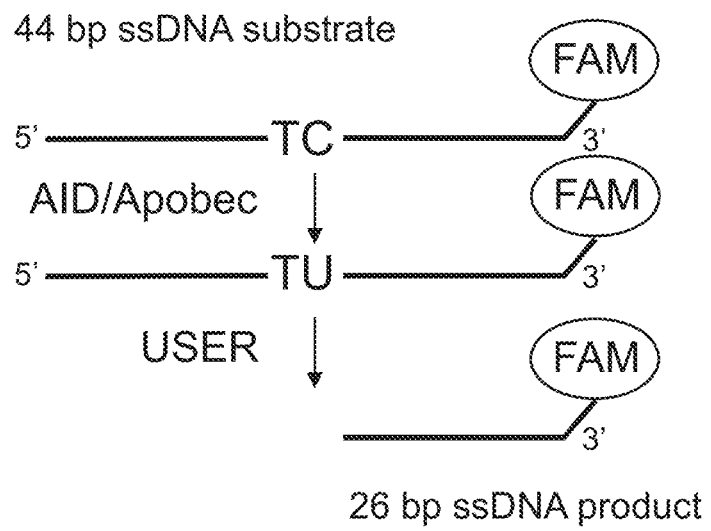

FIG. 2A shows 44 bp single-stranded DNA (ssDNA) substrates having an internal unmodified C adjacent to a T and a 3'-FAM marker. The DNA is reacted with APOBEC-3A that converts a C to a U and with USER™ (New England Biolabs, Ipswich, Mass.). USER removes then cleaves at the U thus generating two fragments where the labeled fragment is 26 bp.

Figure 2B:
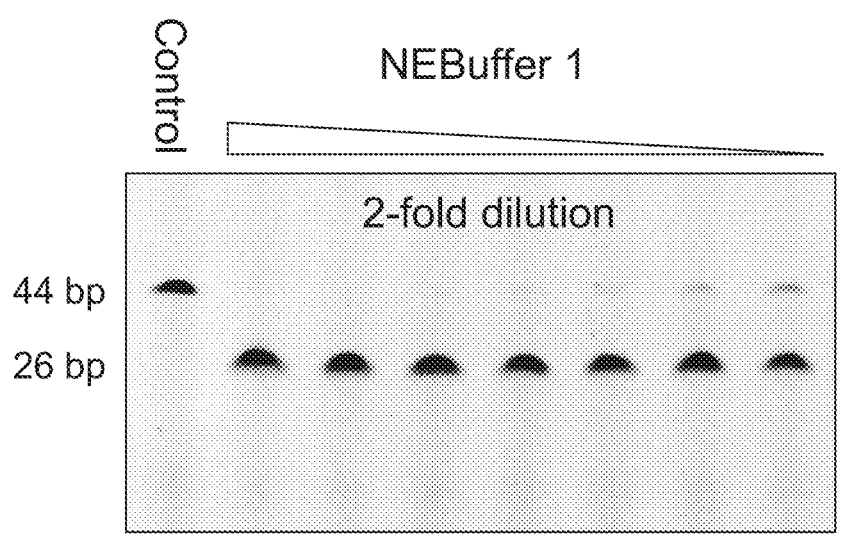
Figure 2C:
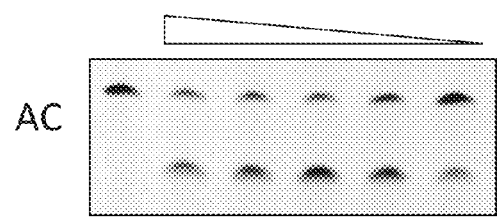
Figure 2D:
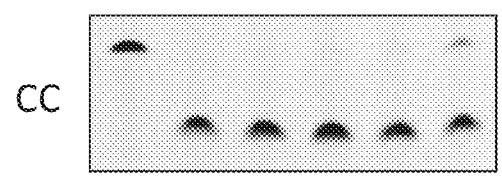
Figure 2E:
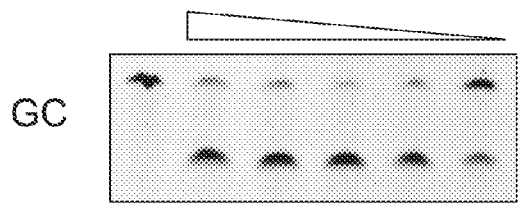
Figure 2F:
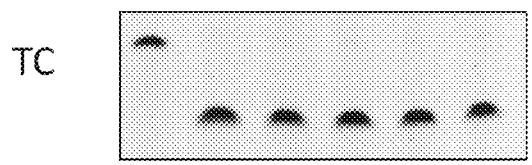

FIG. 2B shows a urea gel which reveals the presence of the 26 bp fragment in all samples except the control which was not reacted with A3A and hence only an uncleaved 44 bp band can be seen.

FIGS. 2C-2F show the cleavage pattern for an APOBEC-3A obtained by in vitro transcription-translation in the PureExpress system. This rapid easy assay shows the extent of deamination of APOBEC-3A for AC (FIG. 2C), CC (FIG. 2D), GC (FIG. 2E) and TC (FIG. 2F) substrates at various concentrations.

Figure 3:
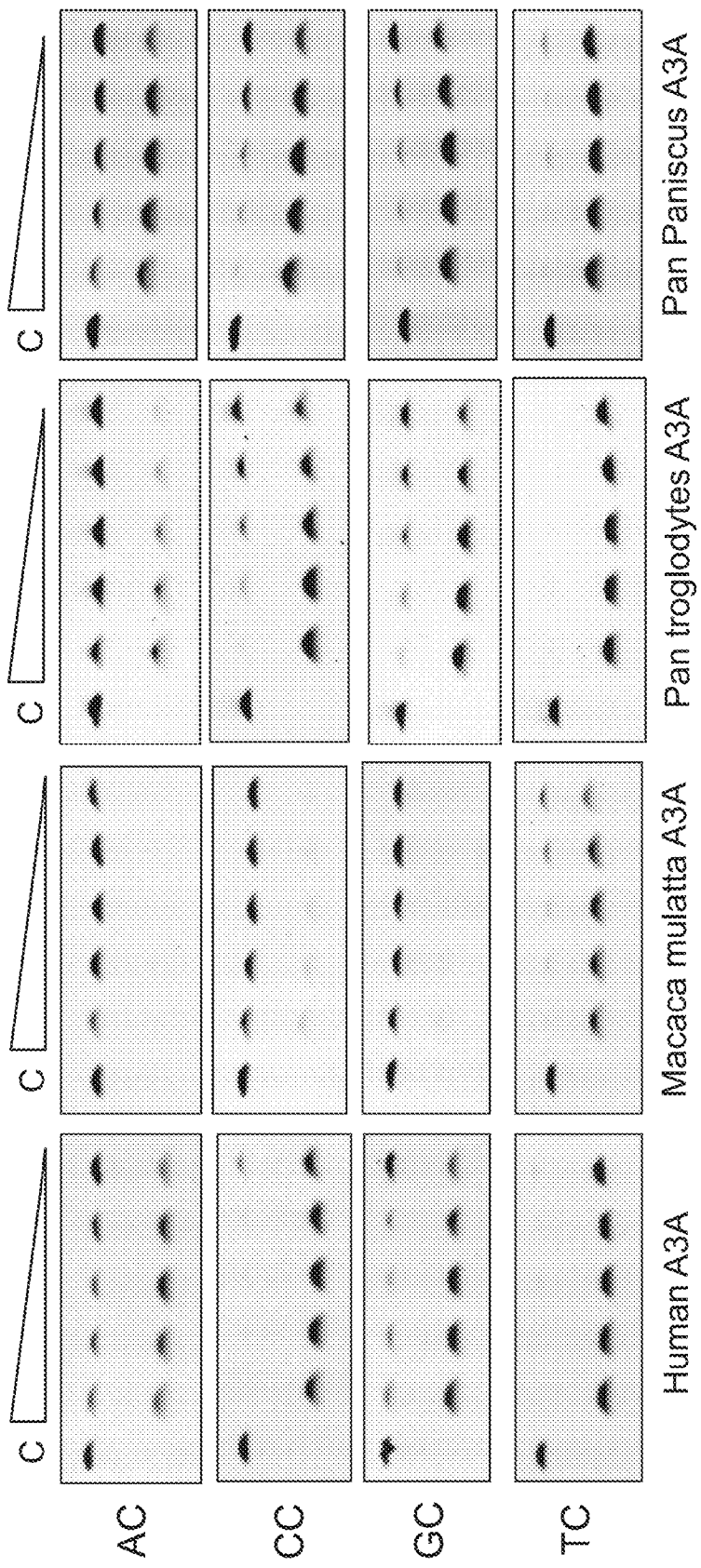

FIG. 3 shows that primate APOBEC-3A family members vary in target sequence preferences: left to right: Human A3A, *Macaca mulatta* A3A, *Pan troglodytes* A3A, and *Pan paniscus* A3A.

Figure 4:
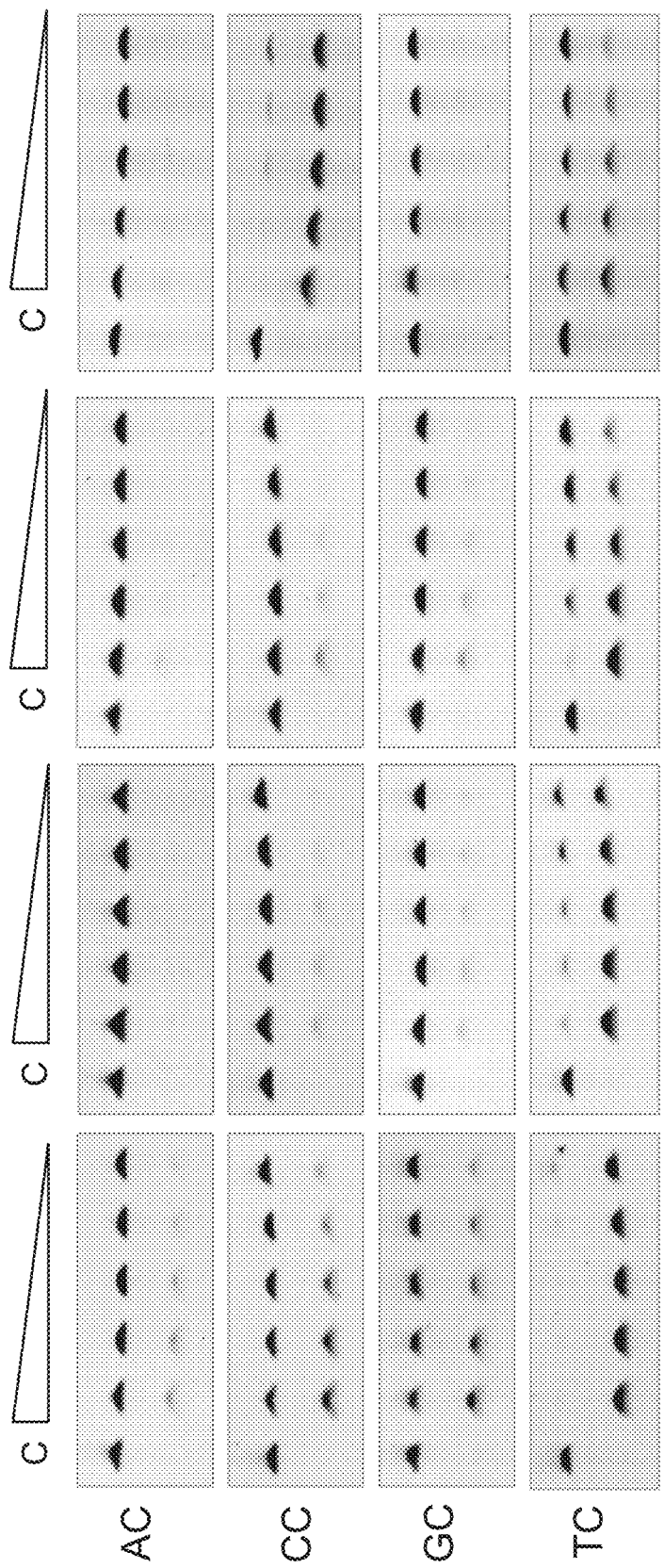

FIG. 4 shows that primate APOBEC-3A family members vary in target sequence preferences: left to right: *Pango pygmaeus* A3A, *Actus trivigatus* A3A, *Hylobates lar* A3A, and *Saimiri sciureus* A3A.

Figures 5A, 5B:
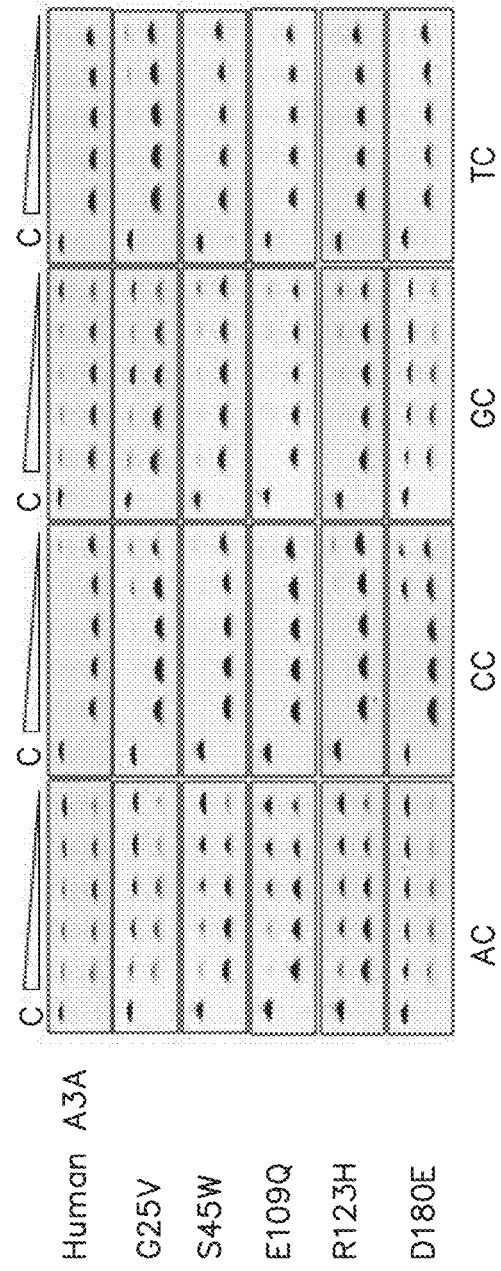

FIG. 5A-B shows that mutations in human APOBEC-3A polypeptide change target sequence preferences.

FIG. 5A shows mutations in the human APOBEC-3A polypeptide sequences that alter target sequence preferences.

FIG. 5B shows activity of mutant enzymes where the mutation is described on the left and the assay is as described in FIG. 2A.

FIG. 5C shows mutations in Pan troglodytes APOBEC-3A that alter sequence preferences.

Figure 5D:
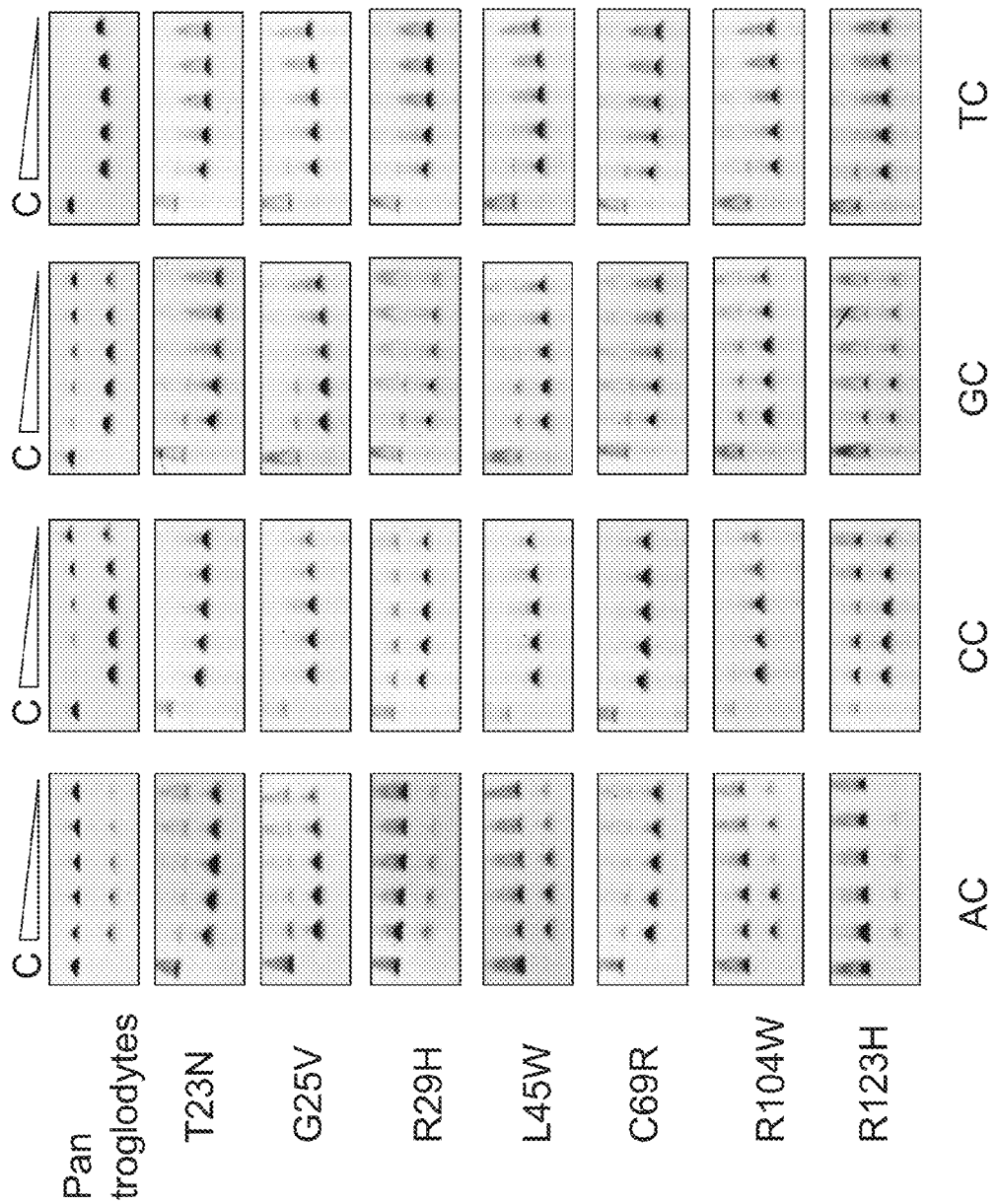

FIG. 5D shows the activity of mutant enzymes where the mutations are listed on the left and cleavage is shown for oligonucleotides containing single AC, CC<GC and TC from left to right using the assay shown in FIG. 2A.

FIG. 6A shows the wild type sequence (SEQ ID NO:3) and a mutant sequence (SEQ ID NO:4).

FIG. 6B shows the AID wild type and an AID mutant described in FIG. 6A and the effect of this mutation on altering target cleavage preferences using urea gel electrophoresis and a substrate an oligonucleotide having a single C immediately preceded by an A.

Figure 7A:
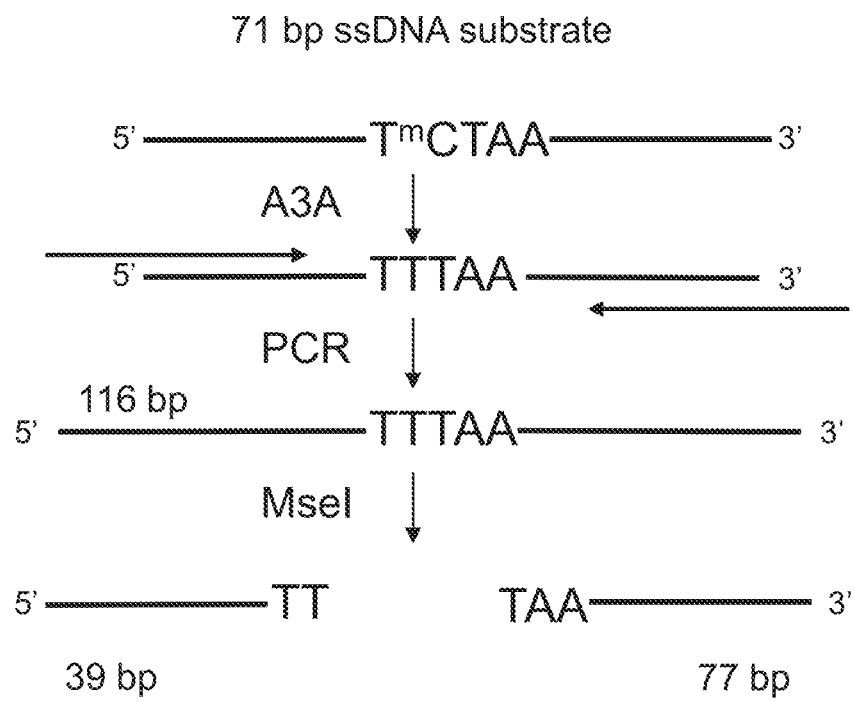
Figure 7B:
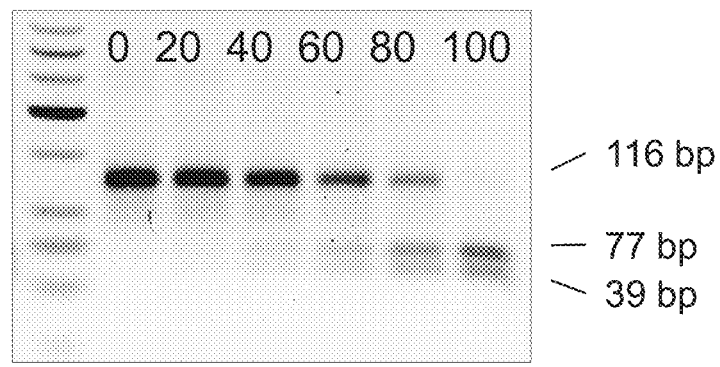

FIGS. 7A and 7B shows an assay for detection of 5-mC in a polynucleotide.

FIG. 7A shows a 71 base ssDNA substrate having an internal T$^m$CTAA that is reacted with APOBEC-3A. Conversion of $^m$C to T by APOBEC-3A and subsequent PCR amplification results in conversion of the sequence to a double-stranded product of PCR containing a TTTAA sequence which can be cleaved by the restriction endonuclease MseI (New England Biolabs, Ipswich, Mass.) (which recognizes TTAA) into two fragments, a 39 base pair fragment and a 77 base pair fragment. The bands can be readily identified using gel electrophoresis.

FIG. 7B shows a gel demonstrating the presence of cleavage products in the form of two reduced molecular weight bands on the gel.

Figure 7C:
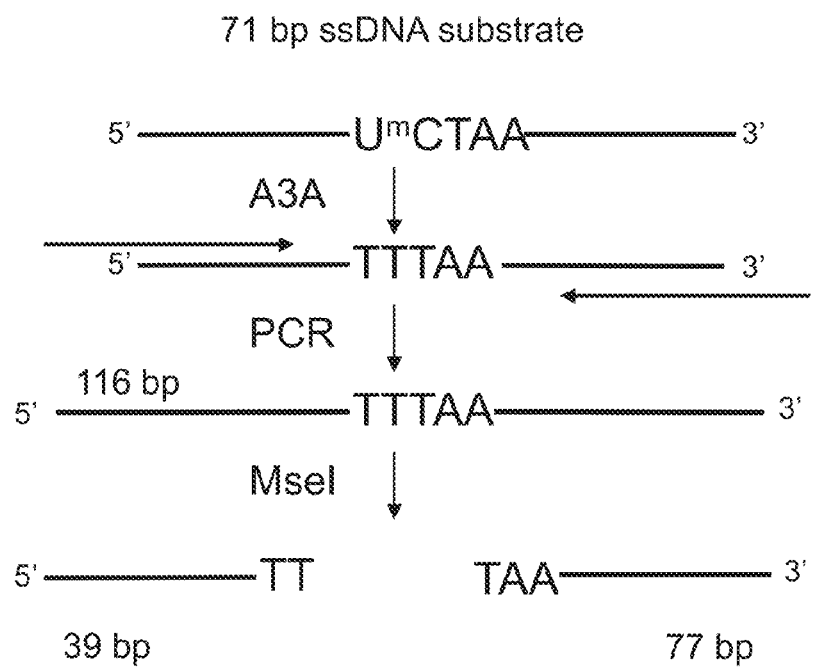

FIG. 7C shows that the ability of a deaminase to convert 5m to T is unaltered in the presence of an adjacent U where the U might arise after conversion from a C to U by a bisulfite sequencing reaction.

Figure 7D:
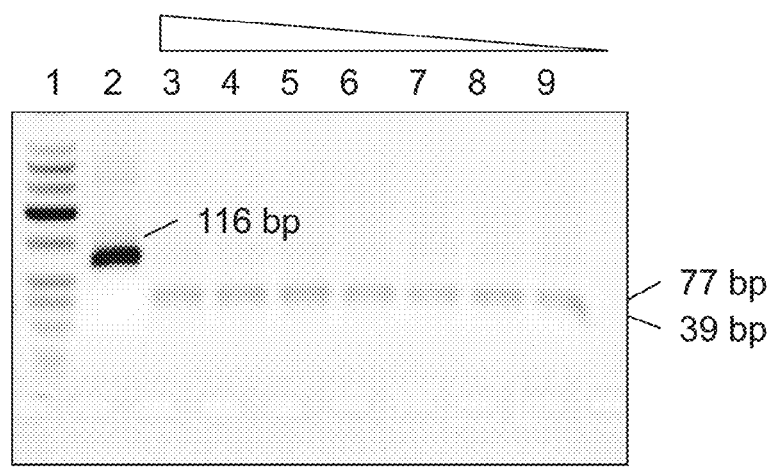

FIG. 7D shows a two-fold serial dilution of APOBEC-3A on the reaction described in FIG. 7C. Lanes 3-9 show 77 bp and 39 bp fragments and no 116 bp DNA demonstrating complete conversion of 5-mC to T.

Figures 8A, 8B:
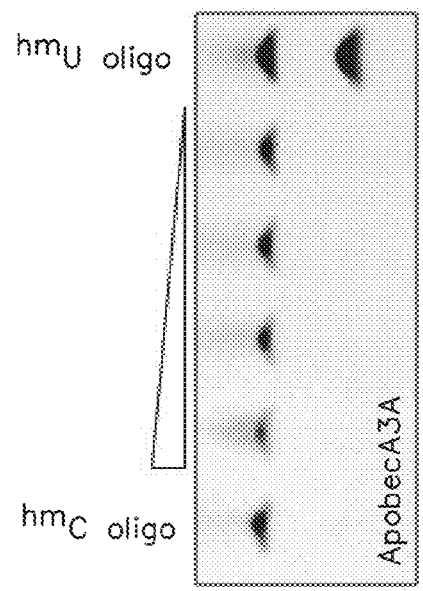

FIGS. 8A and 8B shows that 5-hmC is recognized as a C in the presence of APOBEC-3A.

FIG. 8A provides the labeled single-stranded polynucleotide synthesized with a 5-hmC or hydroxymethyl uracil (5-hmU).

FIG. 8B is a gel which shows that in the presence of USER, only the control polynucleotide containing 5-hmU was cleaved into two fragments. The polynucleotide with 5-hmC remained intact for all enzyme concentrations tested.

Figures 9A, 9B:
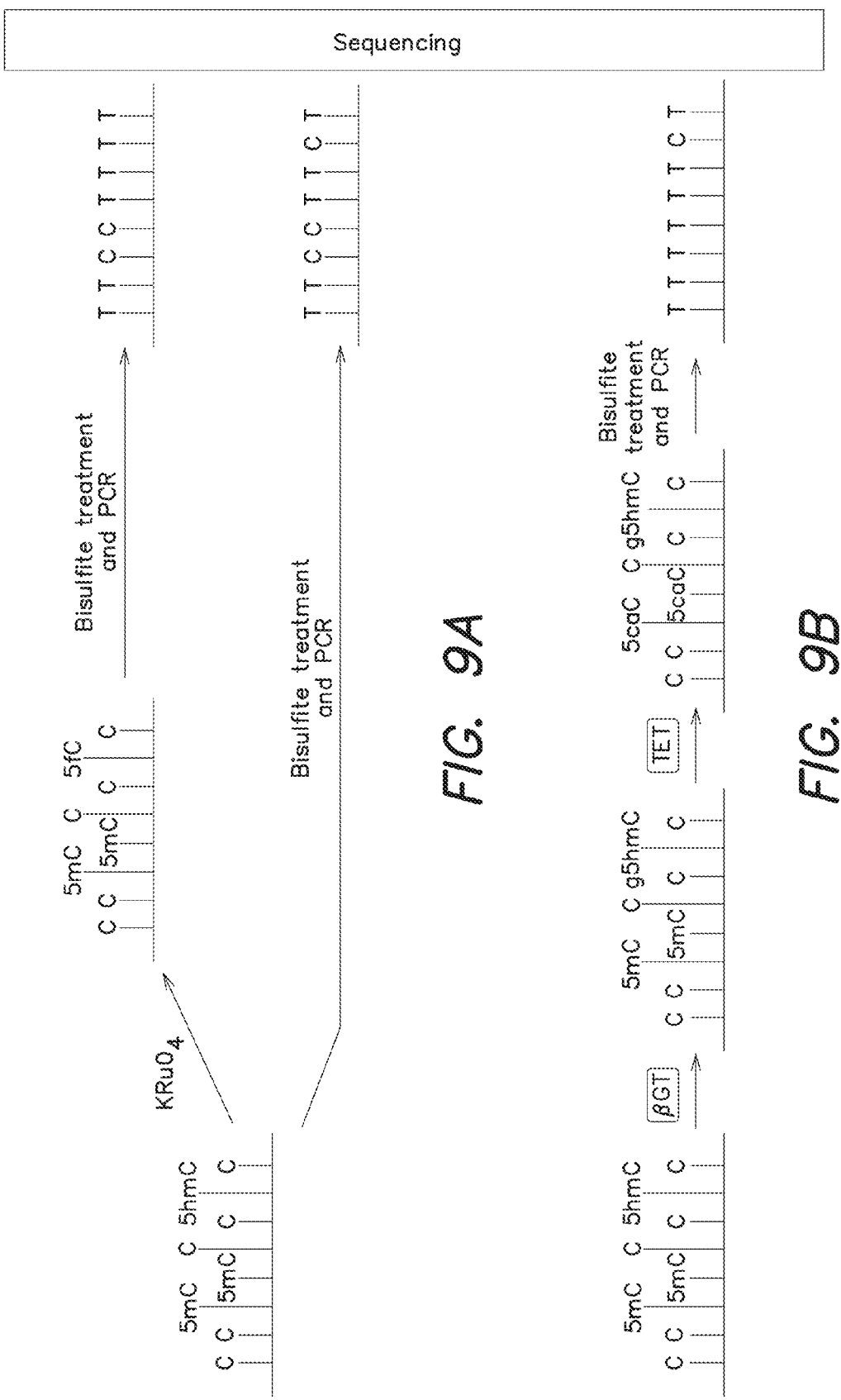

FIG. 9A-B shows prior art methods for identifying 5-mC and 5-hmC residues in a substrate DNA.

FIG. 9A shows a method called OxBS-Seq (Booth, et al. Science, 336.6083:934-937 (2012)). This method requires two bisulfite sequencing steps. In the first sequencing step, 5-hmC in genomic DNA is oxidized to formylcytosine (5-fC) by KRuO4, a reagent that is destructive for DNA. 5-fC is subsequently converted into T by sodium bisulfite treatment. In the second bisulfite sequencing step, genomic DNA is subjected to bisulfite treatment without KRuO4 treatment. The first sequencing step reveals sites of 5-mC; this information is subtracted from the 5-mC plus 5-hmC sites provided by the second traditional bisulfite sequencing step.

FIG. 9B shows a method called TAB-Seq (Yu, et al., Cell, 149:1368-1380 (2012)). This method can distinguish 5-hmC from 5-mC after one bisulfite sequencing step. However, multiple sequential enzyme reactions are required. 5-hmC is selectively protected from TET-mediated oxidation and bisulfite conversion by βGT-catalyzed glucosylation of 5-hmC to glycosylated 5-hmC. Next, 5-mC is oxidized by TET to 5-caC, and subsequently converted into T after bisulfite treatment and PCR. Therefore, TAB-Seq reveals sites of 5-hmC in genomic DNA.

Figure 10A:
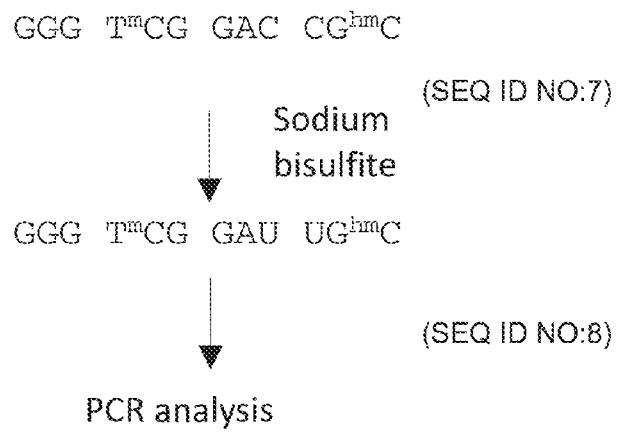
Figure 10B:
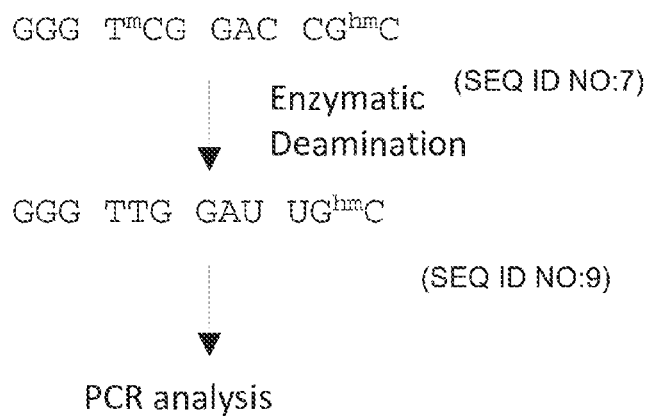
Figure 10C:
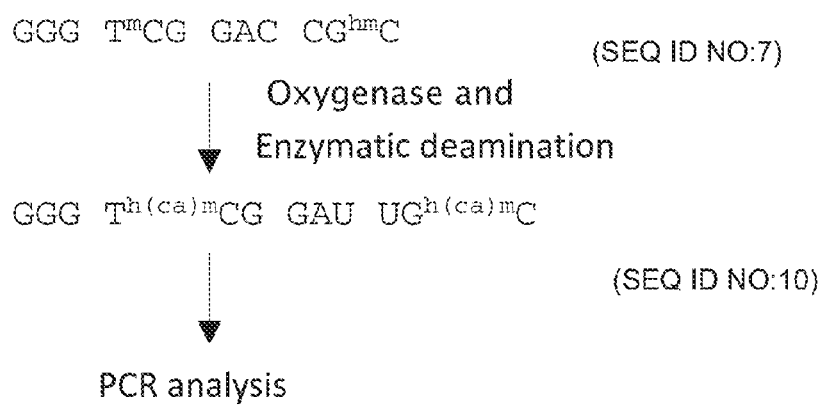

FIG. 10A-C shows an overview of locus specific differentiation of 5-mCs from 5-hmCs in bisulfite converted DNA.

FIG. 10A shows a substrate with C, 5-mC and 5-hmC. Sodium bisulfite sequencing converts the C into U but does not affect 5-mC or 5-hmC.

FIG. 10B shows the same initial substrate as in FIG. 10A except the sample is deaminated using APOBEC-3A or AID so that the 5-mC is converted to a T, the C is converted to a U and the 5-hmC is unchanged.

FIG. 10C shows the same initial substrate as in FIG. 10A but this time, oxidation of the 5-mC and 5-hmC is achieved using TET1 or a methyl pyrimidine oxygenase (mYOX1) to convert the 5-mC and 5-hmC to 5-caC. Sequencing identifies these bases as C.

Figure 11:
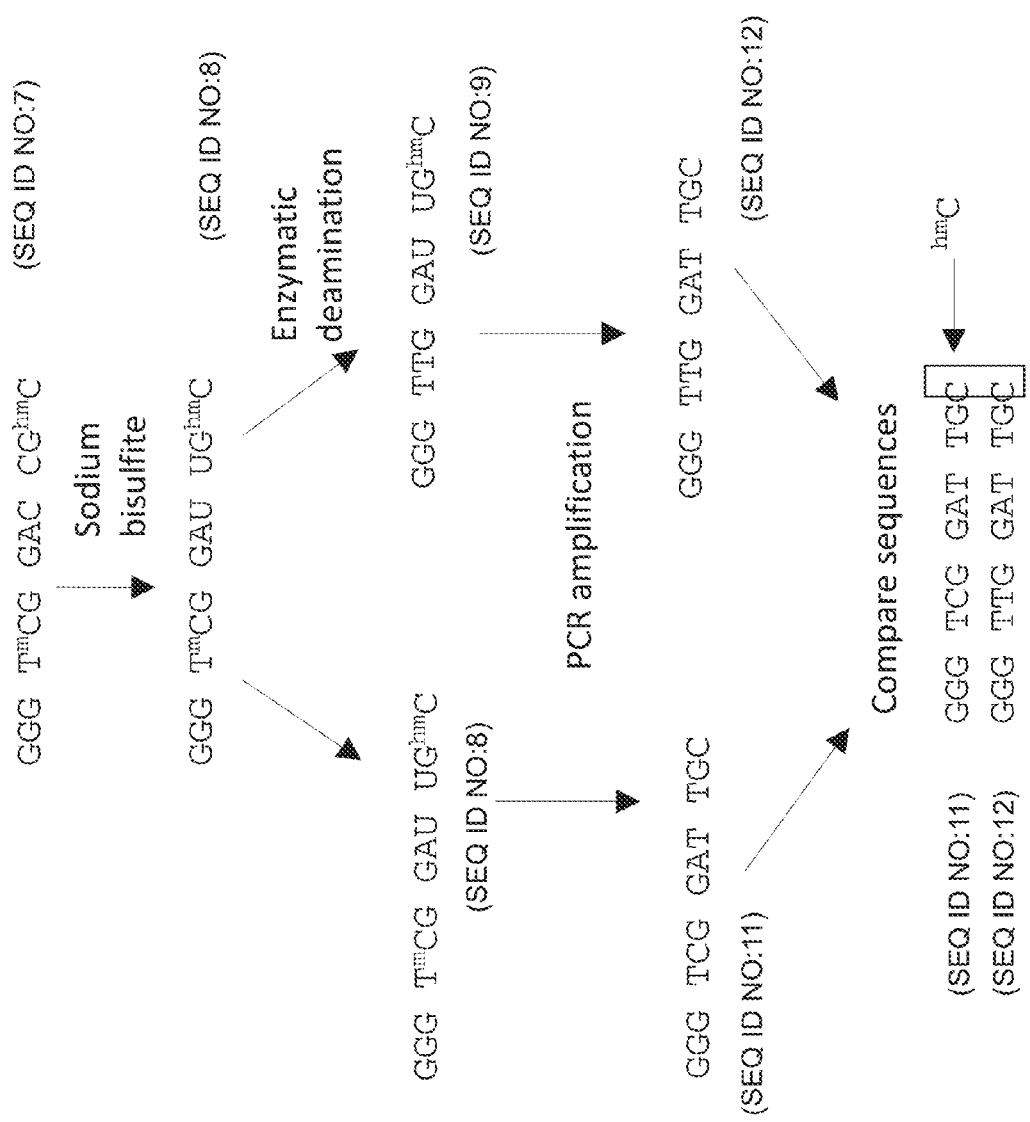

FIG. 11 show a method to detect 5-hmC and 5-mC in a two-step method that first utilizes sodium bisulfite after which the sample is split into two aliquots where one aliquot is not further treated while the other aliquot is deaminated. A comparison of sequences reveals that those Cs in the non-deaminated aliquot that are absent in the deaminated aliquot are 5-mC. Because enzymatic deamination achieves the conversion of C to U, the sodium bisulfite step is optional if it is followed by an enzymatic deamination step.

FIG. 12A-D shows examples of sequences and their fate as they are utilized in the method described in FIG. 10.

FIG. 12A shows a 389 bp substrate in which the methyl CpG are underlined.

FIG. 12B shows a 389 bp substrate where after sodium bisulfite conversion, all Cs converted to Us except methyl in CpG sites.

FIG. 12C shows a 389 bp substrate where after treating with APOBEC-3A enzyme. 5-mCs at CpG sites were converted to Ts.

FIG. 12D shows that after PCR amplification all Us become Ts.

Figure 13:
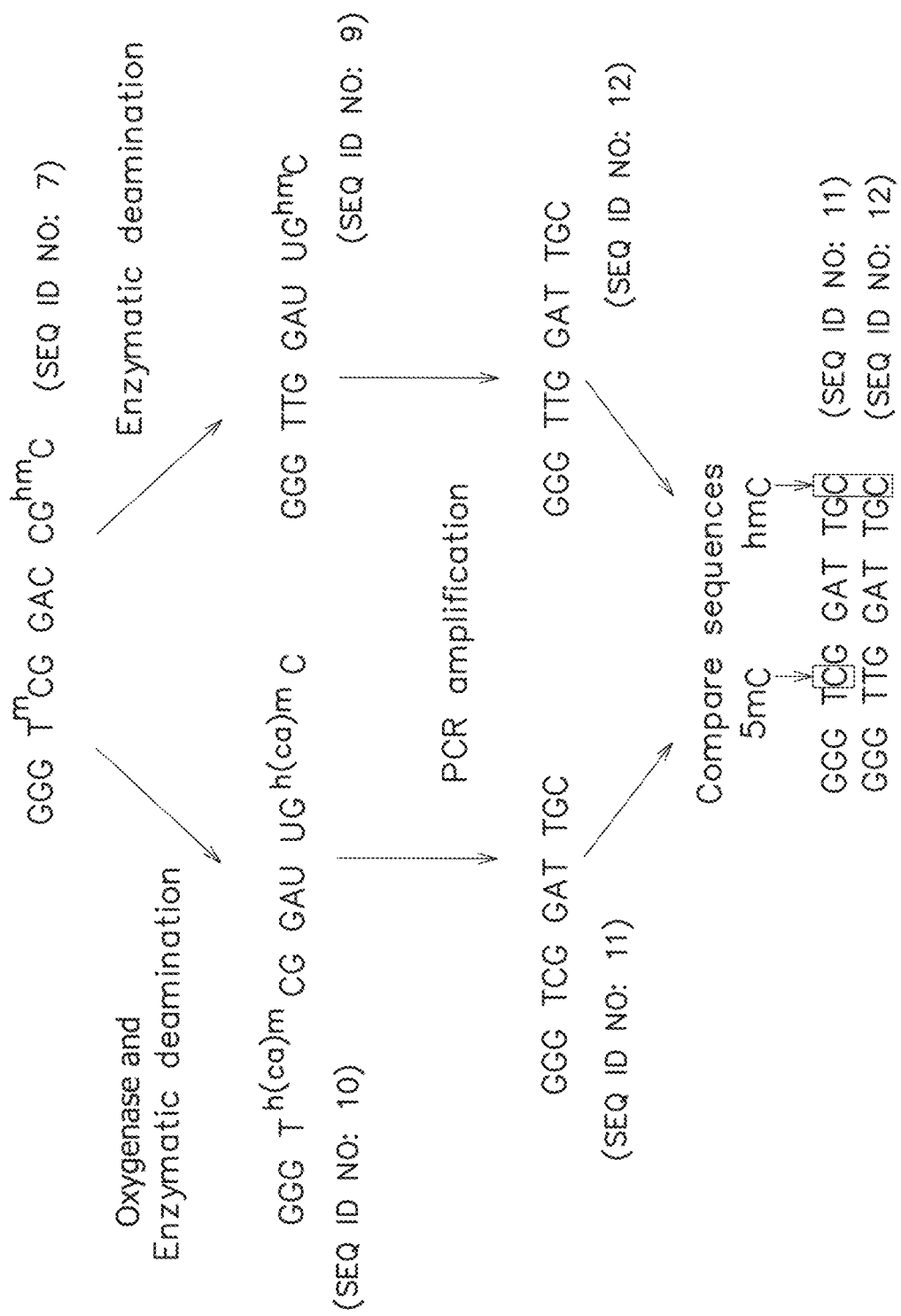

FIG. 13 shows a method for detecting C, 5-mC and 5-hmC in the absence of a bisulfite sequencing step. An oligonucleotide is either reacted with an oxygenase (for example, TET1 or mYOXI) and a deaminase (APOBEC-3A or AID) or with a deaminase alone and then amplified and sequenced. APOBEC-3A converts a C to U but 5-mC and 5-hmC are oxidized to 5-caC which will be identified as C during sequencing. Thus the combination of APOBEC-3A or AID with an oxygenase has the same effect as sodium bisulfite sequencing. If the same oligonucleotide is treated with APOBEC-3A or an AID only then 5-mC will be converted to a T. If the amount of C and 5-mC is known than the sum total of 5-hmC+5-fC+5-caC can be calculated.

DETAILED DESCRIPTION OF THE EMBODIMENTS

The term "cytidine deaminase" is intended to encompass a naturally occurring enzyme, or an enzyme which is not known to be naturally occurring having at least 85%, 90%, 95% and 99% sequence similarity or identity to the wild type enzyme, where the enzyme may be mutated, the mutations optionally including one or more artificially introduced point mutations or deletions.

A wide range of cytidine deaminases have been identified from humans and other species by means of sequence homology. Eleven members of the human APOBEC-3A family are listed in Table 1. The table also lists preferences in recognition of nucleotide motifs, DNA substrate preference for single-stranded DNA (ssDNA) or double-stranded DNA (dsDNA), and biological functions of the enzymes.

The cytidine deaminase family of proteins can be identified in amino acid similarity searches through the occurrence of the ZDD (H/C)-x-E-x25-30P-C-x-x-C. The sequence for human APOBEC-3A is provided in FIG. 5 (SEQ ID NO:1) and human AID is provided in FIG. 6 (SEQ ID NO:3).

The term "oxygenase" includes enzymes that catalyze the conversion of 5-mC and 5-hmC to 5-fC to 5-caC. The family that includes mYOXI is variously referred to as methylpyrimidine oxygenase, a cytosine oxygenase, and a 5-methyl oxygenase. Examples of mYOX include the following:

| Name | Accession # | SEQ ID NO: | SEQUENCE |
|------|-------------|------------|----------|
| mYOX1 | XP_002667965.1 | 24 | MTTFKQQTIKEKETKRKYCIKGTTANLTQTHPNGPVCVNR GEEVANTTTLLDSGGGINKKSLLQNLLSKCKTTFQQSFTN ANITLKDEKWLKNVRTAYFVCDHDGSVELAYLPNVLPKEL VEEFTEKFESIQTGRKKDTGYSGILDNSMPFNYVTADLSQ ELGQYLSEIVNPQINYYISKLLTCVSSRTINYLVSLNDSY YALNNCLYPSTAFNSLKPSNDGHRIRKPHKDNLDITPSSL FYFGNFQNTEGYLELTDKNCKVFVQPGDVLFFKGNEYKHV VANITSGWRIGLVYFAHKGSKTKPYYEDTQKNSLKIHKET K |
| mYOX6 | XP_002674105.1 | 25 | MPMNYITSDLKTQLGEYLIGIVNPMLDETITAALEILSPR TINYLTSLPHPYHILNNCIYPSTAFNYLEPQIEKHRIKNA HKDTRDATPSVLFYLGDYDEKEGYLEFPEQNCKVFVKPGD LLLFKGNKYKHQVAPITSGTRLGLVYFAHKACKVMDFYDD YQKESLNKHKQQNQ |
| mYOX4 | XP_002676528.1 | 26 | MSINTTFNQKTTQSGEPPMMMRMTNSSTPPLTPKNCLPIF VYNDYGKLIREEQQQPTDIITNNNNSMMRSMPTTNRWETN PQTPLSVSPFQPLLPIPNFSHAFIVGNLPPSVSVRRKNRK MSEKPKNNSAPSKIMHQLELSVLNNQRRIAPKGPLADISN IQLPQQESTNKSNNTTPKKPRIRQLMLTTPLRESLQSNQS ARSKYIDEEANNYSINDSPETTIIKTSNTKDSEHKAAMAT NLGLSTDDFECKPFETTTLPSVIDKNYLVVDKEGCTQLAL LPNHIPTSVCKLIEVKCRKVSNLRHALKIQKASFYVNWWT KSQPMGYMCKDNESEIGKVVNEIAELLSDHCRNLLRMCNE RVYKKISELKEDKFFAPCICFNILEHDLESRITKFHHDKM DYGVSVLFYFGDYSRGNLNVLDAGSSSTIVTRPGDAVILR GNYYKHSVCINIEPGNNKARYSIVFFAHSTHFLKKKYELS PAAAKKAFLVDNPDFVSIKKRKQASSSSDVSVKKSKKSTE DNVEFIQTHTYLGNGYKSGHKNYQYYVKFNNSDQKEWKSY ESLPKQAVASYWVKFKKLKSLSNQ |
| mYOX7 | XP_002668594.1 | 27 | MLEAQHHKLTIYTGMWGHMKPCVFIAADNCNKSGETIVEN LLFKLGKIGSKLMEILSPFTMNFLSSLDPEIFLNHDLFPI SATNFMIPGNKHRILKPHKDNQDVGLCIIFYFGNYNAPLE FVNKGSVFNTERGDVLLMRGSHFRHVVKPVDNGLLEHVHD PMRISVVLFAHKSLKMNPSYFLNAGSALKAHDEDFPEKAK KRKKKRK |
| mYOX8 | XP_002676954.1 | 28 | MFLRNILPENTTTEVTNILDKINQRRSKENYYIGSWGKSS SFLFKTNDTIFNELSSQFIKIINLLKNYVLEILKFGNNKM RKFLEKYNSSDFLSIYPTVCFNFLDKSVDENRILHIHPDK EDTGTSLIFYFGKFKGGAISFPELNFKLMVQSADVLLFDG KNNLHAVESLHGKDDVRYSVVFFAHKADLGKTSYPMNRGE VMKGIKNKINN |
| mYOX5 | XP_002668409.1 | 29 | MDIGIDWRGTHFRHKNHLVKEEVCDRTNWIVLCPNGQVDI AFFPNAIPEELCLEMETVVANSDVDILSCKKAIIDGSWTR YGNGIYPVKTITTNQSILLHELNDKCGPFVLDKLKHINKN MFNKLDNINEDIKNYKIFAKYPTLALNVSHNENYNISKKP YRKHTDGNDIGLGVLTYFGSEIIEGGNLIIHIENLKVFNF PIQRRDLVFLNSKFYAHQVTKVTSGIRFGLVYFAGEAHFR VRNNDDFLPALPFNANDKELREERSKKGRKSMNEYKKRFL KKYLREKKKINKKRVKCKNKLK |
| mYOX2 | XP_002682154.1 | 30 | MGPLHVSQHDKKKPKHRRRKKQFLKAQALTRVCWENEKSI DESGKTRVYKMIKEWEFLKGNNIQSNEPILSVYGVNDTIP KEISSNTIIVTKEGMVEMALLKSVLPPSLLEECTQLCREM SEWLATEKDIDKGSFFSGWWTMNMPMGYKCADSFRFELVD TKVKQIQALLHDTFQHILELANPKLFAKLSKLTERGQTPV VCFNMIPTRNESVKEKFQGSYKSTDKVNRPKTNHRDRNDM GISAMFYMGKFGGGSLQLIRVNEHTPKTLVHIQAGDVVLL RANKYRHAVSPTRPQSFPLANSSQTEVDDVKICENSSPTL NNPQADDNTPTLINTCPKQEPTDGDNPVQSSKEPSNDYEQ KRFSFIFFAHRSHFKHSKVYCGMGQRQALNAFKADHPYYQ SQRMKKKLGDDCLDQSLILTEKRKPIKRNYALFNECGDDK QEESDEEEYQQYEPKPTTEEYTIKVIVDHEKVFKGSDQSR KSYLYHIQWLGYPDETWEPYEHLDDCQVFEDYLKHHNISL FDEEEEDRKVDDSMLLPAWMHEDESLFEALLPIICCSTDN PRHHLDDVPPFDFNY |

-continued

| Name | Accession # | SEQ ID NO: | SEQUENCE |
|------|-------------|------------|----------|
| mYOX3 | XP_002668005.1 | 31 | MTEIVELSNIEPKDQKQAIIGGTWNRYGNSIEIVAGISDE NNTLLDNLTNCCESFVLDKLWHLNRSMYNKLDTIEEKIKN FKTYAKYPSLALNLLCKENYNGKVKPYRKHIDPNNNGMDV LMFFGKTFEGGNLIVSYHYTNIDFRMFTLPIQSGDLVFLN SRIYHHKVTKVTSGVRCGLVFFAGLDHFSVRKANYKKVKK EEYQKNMDDKLLALPFQQKDKDLRIERTKTGRKEIKQFHK NLQNNLPNKKRKK |

The term "polynucleotide" includes a DNA or RNA having ranging in size from a few nucleotides (for example, 10 nucleotides) to a genome length. A polynucleotide as used herein may also be 1 kb or 2 kb or 5 kb or 10 kb in length unless otherwise specified.

The term "DNA polymerase" includes any polymerase suitable for amplifying DNA by isothermal or temperature cycling amplification methods.

In general "detecting", "determining" and "comparing" refer to standard gel based techniques such as SDS gels or TBE-urea gels described in the examples and equivalent methods well known in the art. These terms may be applied to sequencing, where DNA sequences are compared. There are a number of sequencing platforms that are commercially available and any of these may be used to determine or compare the sequences of polynucleotides.

The term "sodium bisulfite sequencing reagents" refers to a standard method for detecting 5-mC as is described in Frommer, et al., *Proceedings of the National Academy of Sciences*, 89.5:1827-1831 (1992).

A number of problems had to be solved to achieve the present embodiments. These include:
(a) a means to generate sufficient quantities of purified APOBEC-3A/AID to test reproducibly for deamination specificity;
(b) a simple, reliable assay was developed to determine whether the activity and specificity of an cytidine deaminase or its homolog or derivative might be suitable for the desired purpose; and
(c) determination of whether and to what extent any purified cytidine deaminase obtained from a natural source could deaminate a C adjacent to an A, T, G or C.

Means for Generating Sufficient Quantities of Purified APOBEC-3A

An in vitro transcription and translation system was successfully utilized to generate purified active APOBEC-3A and AID from a synthetic gene sequence. The product of synthesis could then be tested on synthetic oligonucleotide substrates containing a modified C in varying sequence contexts. The sequences of the oligonucleotides can be essentially any sequence containing a C or modified C although in embodiments of the assays, the oligonucleotide preferably has a single C unless otherwise specified with an alternative base immediately preceding the C. FIGS. 8-11 show that APOBEC-3A and AID express well in in vitro transcription translations systems.

An Assay for Cytidine Deaminases

Synthetic oligonucleotide substrates were prepared which contain a single internal C and a 3' label (Integrated DNA Technologies, Coralville, Iowa). A synthetic oligonucleotide with multiple internal Cs may also be used as a substrate, to generate multiple fragments in the assay described in FIG. 2. A synthetic oligonucleotide can be substituted by a naturally occurring DNA fragment which is denatured so as to provide single-stranded fragments suitable for reacting with APOBEC-3A and AID. Using substrates designed as described above, assays were designed to: (a) analyze the specificity of an APOBEC-3A or AID or variant thereof; (b) differentiate C from 5-mC; and (c) differentiate 5-hmC from 5-mC.

(a) Use of a cleavage agent for breaking ssDNA into 2 fragments at a cytidine deaminase modified nucleotide.

This assay for determining the activity of a cytidine deaminase relies on a change in a ssDNA that results in selective cleavage using a reagent. Although the detectable marker illustrated in FIG. 2A and FIG. 2B and in Example 2 was a fluorescent label, any label known in the art capable of attaching to the 3' end or the 5' end of an oligonucleotide and being detectable on a gel or other separation device, can be used. Examples of detection labels and capture tags for oligonucleotides are described in U.S. Pat. No. 6,368,801.

The conversion by APOBEC-3A or AID of a C into a U can be detected rapidly and simply by reacting the oligonucleotide with a glycosylase/endonuclease mixture such as the commercially available USER or an equivalent which removes the U from the DNA thereby generating two fragments from the oligonucleotide, one of which retains the fluorescent label. Since the labeled cleavage product is significantly smaller than the full-length oligonucleotide, it can readily be detected by size separation such as shown using gel electrophoresis. FIGS. 3 and 4 show assay results for 8 human and simian APOBEC-3A enzymes using the rapid assay shown in FIG. 2 on PURExpress generated samples. An advantage of this assay and others that utilize cytidine deaminase is that the temperature of the reaction may be less than 60° C. for example, less than 50° C., or less than 40° C.

(b) Restriction endonuclease cleavage of dsDNA only after cytidine deaminase induced modification of a C to a T.

A change of a C to a T in a reaction with APOBEC-3A or AID was designed to result in the formation of a specific restriction endonuclease cleavage site that was not present previously. When this modified oligonucleotide was amplified, the resulting dsDNA could be cleaved by the restriction endonuclease to generate two fragments where previously only one was present. Example 3 and FIG. 7A-D describe one instance of this method. PCR amplification is described here though any form of amplification can be used including various isothermal amplification methods such as transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification, and circular helicase-dependent amplification.

(c) Conversion of 5-hmC to 5-hmU.

The oligonucleotides were reacted with a cytidine deaminase so that the 5-hmC was converted to 5-hmU. 5-hmU could be cleaved with a glycosylase and an endonuclease. In the example, SMUG (New England Biolabs, Ipswich, Mass.) was used with EndoVIII (New England Biolabs, Ipswich, Mass.) to cleave the synthetic oligonucleotide. A cleavage fragment could be detected by a label either at the 3' end or the 5' end of the oligonucleotide although a same, similar or different label could be used at either end of the oligonucleotide substrate to facilitate detection of the cleavage product. Example 4 and FIG. 8 show results obtained using a 3'FAM label on a synthetic oligonucleotide with a single internal 5-hmC located in a sequence TCT in a substrate oligonucleotide and treated with APOBEC-3A.

The ability to readily make protein variants and the robust assay both described herein, provides a simple means to generate and evaluate mutants of cytidine deaminases for improved catalytic conversion of C and 5-mC in polynucleotide substrates that may be ssDNA fragments or genomes. An advantage of the methods described herein are that they are suited for analyzing large pieces or even entire genomes without the difficulties of shearing that arise when a temperature or alkali denaturation step is required or where the chemical also cleaves the DNA, as in bisulfite sequencing.

Mutants of APOBEC-3A and AID were generated that had enzymes with reduced or no bias to any particular sequence context for converting a C to U or a 5-mC to T. For example, using a human APOBEC-3A sequence as a starting point, mutations were introduced into the gene and the mutants tested in the assay described above. The results for 12 mutants of two wild type APOBEC-3A are shown in FIGS. 5A-D and for 1 mutant of AID in FIG. 6A-B. These mutations are intended to be representative and are not intended to be comprehensive. It would be straightforward based on the compositions and methods described herein to select a sequence of a cytidine deaminase such as APOBEC-3A from a sequence database, introduce mutated amino acids into the protein sequence and assay for altered substrate specificity using embodiments of the methods described here.

Various combinations of the 5 mutants of human APOBEC-3A and 7 mutants of Pan troglodytes APOBEC-3A are shown in the examples and in FIG. 5A-D that have altered cleavage bias of substrates. For example, for human APOBEC-3A, E109 could be combined with one or more of any of G25, S45, R123 and D180, for example E109A could be combined with one or more of any of G25V, S45W, R123H and D180E. Similarly, R123 could be combined with one or more of any of E109 G25, S45, and D180 for example, R123H could be combined with one or more of any of E109Q G25V, S45W, and D180E. Similarly, D180 could be combined with one or more of any of G25, S45, R123 and E109 for example D180E could be combined with one or more of any of G25V, S45W, R123H and E109Q. Similarly, S45 could be combined with one or more of any of G25, E109, R123 and D180 for example S45W could be combined with one or more of any of G25V, E109Q, R123H and D180E. Similarly G25 could be combined with one or more of any of E109, S45, R123 and D180 for example G25V could be combined with one or more of any of E109Q, S45W, R123H and D180E. In one example, human APOBEC-3A with an E190 mutation for example E109Q was used in embodiments of the method. In another example human APOBEC-3A with G25, S45, E109, R123 and D180 mutations for example G25V, S45W, E109Q, R123H and D180E mutations were used.

For Pan troglodytes APOBEC-3A, one or more of mutations at positions corresponding to 23, 25, 29, 45, 69, 104 and 123 can be introduced into (SEQ ID NO:2) to alter the sequence preference for the enzyme. Examples of specific mutations correspond to 23N, 25V, 29H, 45W, 69R, 104W and 123H. Examples of combinations of mutations include combining a mutation at positions corresponding to 23 with one or more or two or more mutations at positions corresponding to 25, 29, 45, 69, 104 and 123; or 25 with 29, 45, 69 104 and 123, or 29 with 45, 69, 104 or 123, or 45 with 69, 104 or 123, or 69 with 104 or 123, or 104 with 123. Three or more or four mutations selected from positions corresponding to 23, 25, 29, 45, 69, 104 and 123 can be selected or a mutant may be constructed that includes 5 mutations at positions corresponding to 23, 25, 29, 45, 69, 104 and 123 for example 23N, 25V, 29H, 45W, 69R, 104W and 123H.

With the disclosed assay, it is possible to mutate any cytidine deaminase at any site and test the mutant for altered site preference. In one embodiment of the invention, a cytidine deaminase with a site preference is selected to determine the locations of a subset of 5-mC residues present in a target nucleic acid.

In another embodiment of the invention, a cytidine deaminase with little or no site preference is preferred. Accordingly, a mutated APOBEC-3A having a mutation corresponding to E109Q or S45W from SEQ ID NO:1 or C69R, T23N, or G25V in SEQ ID NO:2 may be selected with these features.

Mutants of wild type AID (SEQ ID NO:3) were created and can be used in embodiments of the methods described herein. For example a mutation at position 117 may be introduced, for example a deletion as shown in FIG. 6A (SEQ ID NO:4).

In one embodiment, a method is provided which shows a time course leading to complete conversion to U of all 5-mCs in a substrate containing multiple 5-mCs which when amplified resulted in a T in place of a U (see for example FIG. 8A-8B). APOBEC-3A is demonstrated to convert all of the 5-mC into U in a time that is greater than 2 hours although even after 1 hour about 95% is converted. It is expected that manipulating conditions such as one or more of pH, concentration and buffer and selected APOBEC-3A or AID variants results in substantially 100% conversion in a time frame of less than 2 hours.

Methylome Sequencing

Sodium bisulfite sequencing has become an established method for mapping 5-mC in a genome as part of an epigenetic study. Unfortunately, sodium bisulfite sequencing cannot differentiate between 5-mC and intermediates of demethylation such as 5-hmC, 5-fC and 5-caC. In brain tissue, there is a significant amount of 5-hmC as well as small amounts of 5-fC and 5-caC while in all tissues, there are at least some of these modified bases. Another problem associated with sodium bisulfite sequencing is that the method damages the target DNA causing extensive fragmentation. This complicates assembly of maps for a methylome. Another problem of sodium bisulfite sequencing is that it involves multiple chemical steps and therefore is intrinsically inefficient and costly to perform. Nonetheless, an embodiment of a method is provided that facilitates sodium bisulfite sequencing and ameliorates one or more of the above limitations. Accordingly, a one-enzyme step enables mC to be differentiated from a 5-hmC (see FIG. 11).

The sodium bisulfite reaction which precedes the deamination reaction was shown not to interfere with this reaction (see FIG. 11).

Embodiments of the invention include methods for methylome construction that may utilize sodium bisulfite sequencing while reducing the number of steps to determine not just the occurrence of modified bases but the occurrence of methyl bases and not hydroxymethyl bases. Other embodiments do not utilize sodium bisulfite sequencing at all but rather utilize two enzyme reactions, in particular, a demethylase such as methyl-pyrimidine oxygenase or TET or analog thereof and an AID. A comparison between these oxygenases is given below. An example of the class of enzymes referred to as methyl pyrimidine oxygenases is an enzyme identified as mYOXI which is described in U.S. application Ser. No. 13/827,087.

TABLE 1

Properties of oxygenases

| Name | Methyl-pyrimidine oxygenase | 5-methylcytosine oxygenase (TET) |
|---|---|---|
| Length | ~300AA | ~1600AA |
| Reaction temp. | 34 C. | 37 C. |
| Cofactors | 2-oxoglutarate and $Fe^{2+}$ | 2-oxoglutarate and $Fe^{2+}$ |
| Optimal pH | 6-6.5 | 8 |
| Substrate forms | DS-DNA, SS-DNA | DS-DNA |
| Substrate | 5-mC (and depending on enzyme, T) | 5-mC |
| Products | 5-mC->5-hmC/5-fC/5-caC, T->5-hmU/5fU/5-caU | 5-mC->5-hmC/5-fC/5-caC |
| Substrate specificity | Converts mCG to >90% 5-caC, coverts mCWG to a mix of 5-hmC/5-fC/5-caC | Similar to mYOX1 |
| ATP effect | Inhibition | stimulation |
| Conserved Sequence feature | Contains characteristic 2OGFE-domains, presumably for binding 2OG and $Fe^{2+}$ | In addition to 2OGFE-domains, there are long extra sequences. |

FIG. 10A-C shows a comparison of: sodium bisulfite sequencing in which an unmodified C is deaminated to form a U leaving 5-mCs detected as a C (FIG. 10A); enzymatic deamination only (FIG. 10B) in which an unmethylated C is converted to U, a 5-mC is converted to a T and no change is observed with 5-hmC which is read as a C in the sequencing reaction; and with an oxygenase reaction step (FIG. 10C) in which a 5-mC and 5-hmC are converted to 5-caC which is recognized as C and thereby replicates the sodium bisulfite sequencing reaction. When parallel reactions are analyzed for samples+/−enzymatic deamination, after sodium bisulfite sequencing step, the results reveal which C residues were methyl and which were hydroxymethyl by subtraction (FIG. 11).

The reaction pathways in FIG. 13 remove the need for a sodium bisulfite sequencing reaction. This method contrasts with TAB-seq (Yu, et al. (2012)) which requires two separate enzyme reactions in addition to sodium bisulfite sequencing. In TAB-seq, 5-hmC is first labeled with a glucosyl transferase, and 5-mC is oxidized prior to sodium bisulfite sequencing to 5-caC which is then converted to 5-caU and hence to T (see FIG. 9A-B).

TABLE 2

A summary of the human cytidine deaminase family of enzymes.

| APOBEC-3A | HotSpot motif | Substrate | Function |
|---|---|---|---|
| AID | WRC | ssDNA | Somatic hypermutation Class switch recombination |
| Apo1 | G/CTC | ssDNA | Lipid metabolism |
| A3A | T/CCA | ssDNA | Inhibits parvovirus, HPV, retroelements |
| A3B | C/GTC | ssDNA | Inhibits HIV, HBV, retroelements |
| A3C | TC/TC | ssDNA | Inhibits HBV, HPV, retroelements |
| A3DE | WWC | ssDNA | Inhibits HIV |
| A3F | TTC | ssDNA | Inhibits HIV, HBV, retroelement |
| A3G | CCC | ssDNA | Inhibits HIV, HBV, retroelement |
| A3H | unknown | unknown | Inhibits HPV |
| Apo4 | unknown | unknown | unknown |

All references cited herein including U.S. application Ser. No. 13/827,885 filed Mar. 14, 2013 and U.S. Provisional Application No. 61/611,295 filed Mar. 15, 2012 are incorporated by reference.

EXAMPLES

Example 1: Synthesis of APOBEC-3A, AID and Mutants Thereof Using PURExpress

The AID and APOBEC-3A DNA sequences were codon optimized and reverse synthesized to form the gene sequence. The synthesized DNA was subcloned by TOPO®

Figure 1:
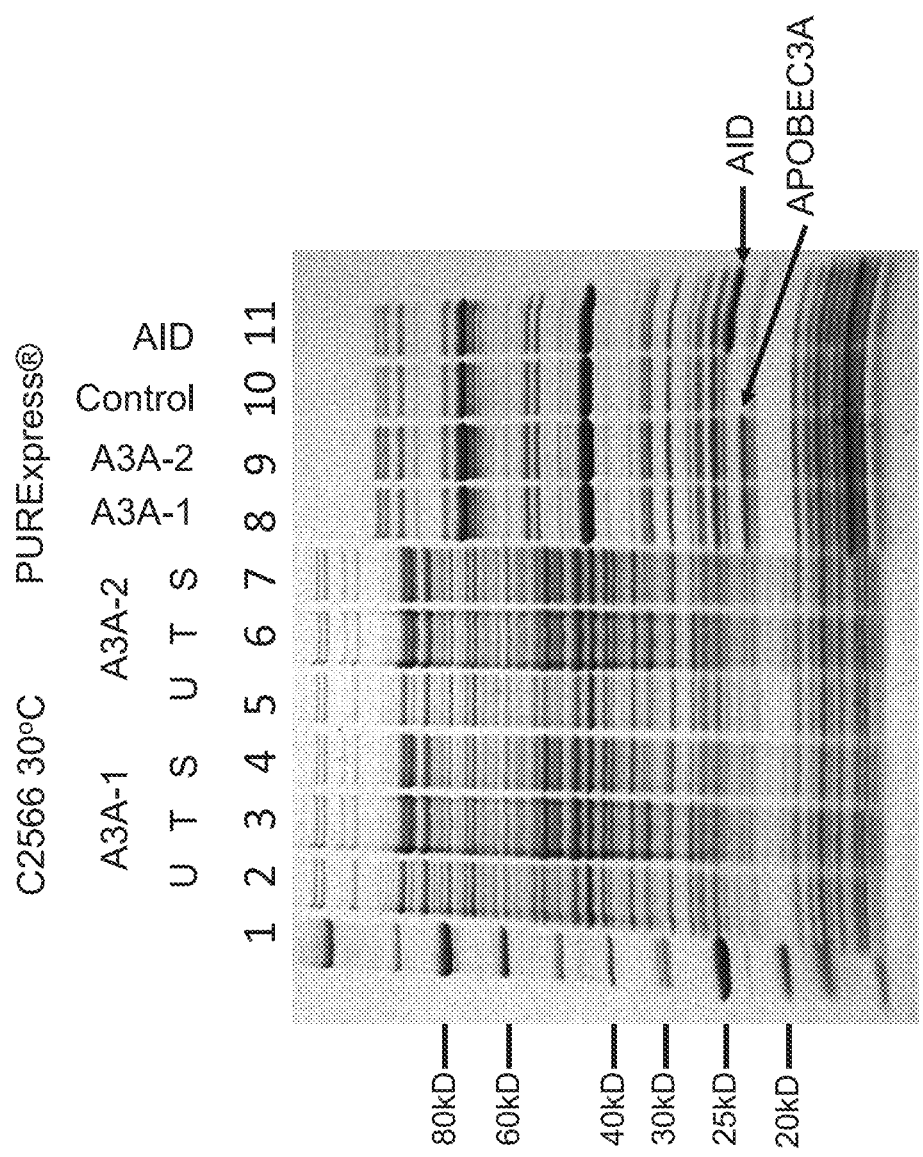
FIG. 1 shows that APOBEC-3A expresses well in a cell-free transcription translation system (PURExpress®, New England Biolabs, Ipswich, Mass.) compared with *E. coli* transformed with DNA encoding APOBEC-3A which did not produce a detectable amount of protein as determined by gel electrophoresis.

TA Cloning® (Life Technologies, Carlsbad, Calif.) under a T7 phage promoter and inserted into NEB 5-alpha F'/$^q$ Competent *E. coli* (New England Biolabs, Ipswich, Mass.). Mutant proteins were produced with the Q5® Site-Directed Mutagenesis Kit (New England Biolabs, Ipswich, Mass.) before being subcloned as above. 200 ng of each plasmid was used as template for in vitro synthesis of AID, APOBEC-3A, or their mutants using PURExpress. The in vitro reaction was incubated at 37° C. for 5 hours, and the synthesized proteins were boiled for 3 minutes, and after precipitation by centrifugation, a sample of the supernatant was loaded on an SDS gel. The results are shown in FIG. 1.

Example 2: Biochemical Assay for Cytosine Deamination (See FIG. 2)

TABLE 3

The following components were combined in a 1X solution to convert C to U:

| Reaction Component | Volume, μl | Stock | Final Concentration |
|---|---|---|---|
| Nuclease-free water | 15.8 | | Total volume: 20 μl |
| Oligonucleotide | 1 | 1 μM | 50 nM |
| RNase A | 0.2 | 10 mg/ml | 1 μg |
| NEBuffer 1 (New England Biolabs, Ipswich, MA) | 2 | 10x | 1x |
| PURE extract (APOBEC-3A/AID | 1 | | 50 ng |

The oligonucleotide was synthesized with a FAM label (Integrated DNA Technologies, Coralville, Iowa). The reaction mixture was incubated at 37° C. for 1 hour, and 10 μl of 1× NEBuffer 1 were added, containing 0.5 μl (0.5 U) of USER, and incubated additional 30 minutes at 37° C.

The products were separated on a 15% TBE-Urea gel (Invitrogen, Grand Island, N.Y.) using the XCell SureLock® Mini-Cell (Invitrogen, Grand Island, N.Y.).

Serial dilutions were performed on samples in order to determine the activity of AID, APOBEC-3A, or their mutants in a fixed ratio (such as 1:1, 1:2, 1:4, 1:8, etc.) as indicated below:

TABLE 4

Components were combined in a 1X solution or a titration assay of the selected deaminase

| Reaction Component w/o deaminase | Volume, μl | Stock | Final Concentration |
|---|---|---|---|
| Nuclease-free water | 16.8 | | Total volume: 20 μl |
| Oligonucleotide | 1 | 1 μM | 50 nM |
| RNase A | 0.2 | 10 mg/ml | 1 μg |
| NEBuffer 1 | 2 | 10x | 1x |

1 μl of APOBEC-3A or AID (wild type or mutant) after in vitro transcription/translation using PURExpress (containing about 50 ng of DNA deaminase enzyme) was added to the first tube in the serial dilution (1:1) which then contained 40 μl of the reaction mixture with deaminase (1× solution). 20 μl from the first tube was placed into 20 μl of reaction components without enzyme in a second tube (1:2) and so forth for the desired numbers of dilutions resulting in 2×, 4×, 8×, 16× and 32× dilutions (1×) in a reaction volume of 20 μl. The reaction mixture was incubated at 37° C. for 1 hour, and 10 μl of 1× NEBuffer 1 were added, containing 0.5 μl (0.5 U) of USER, and incubate additional 30 min at 37° C. The products were separated on a 15% TBE-Urea gel using the XCell SureLock Mini-Cell.

Generation of Mutants

The APOBEC3A or AID mutants were generated by random mutagenesis or site-specific mutagenesis.

For random mutagenesis the error-prone PCR method according to Cirino, et al., *Methods in Molecular Biology*, 231:3-10 (2003), was used; although the $MgCl_2$ concentration was increased to 7 mM concentration in the reaction.

For site-specific mutagenesis, the Q5® Site-Directed Mutagenesis Kit (New England Biolabs, Ipswich, Mass.) was used following the manufacturer's instructions. Target residues were selected according to sequence conservation, or predicted location in loop domains (Kohli, et al., *Journal of Biological Chemistry*, 284.34:22898-22904 (2009)) The mutant proteins were manufactured in cell-free PURExpress® system (see Example 1) and tested for activity as described above in Examples 2 and 3.

Example 3: APOBEC-3A Activity Assay on 5-mC Containing Substrate

A. Biochemical Assay for 5-mC Deamination

The following components were combined in a 1× solution. The following components were combined in a 1× solution in order to convert 5-mC to T (and C to U) in the oligonucleotide.

TABLE 5

Reaction components for 5-mC deamination

| Reaction Component | 1x |
|---|---|
| Nuclease-free water | 16.5 |
| Oligonucleotide * (1 μM) | 1 |
| RNase A (100 μg/ml) | 0.2 |
| NEBuffer 1 (10x) | 2 |
| PURE extract | 0.3 |

\* TATGGGGAAGGTTAGGGAAGATAAGAATAGAATGAAT/iMe-dC/GAAGGAT-GAATATGAGGTGAGGAGTAGGATGGG (SEQ ID NO: 17)
iMe-dC = 5-methylcytosine The reaction mixture was incubated at 37° C. for 12-16 hours, or overnight, and PCR reaction was performed followed by MseI digestion.

TABLE 6

PCR reaction components

| Component | 50 μl 1x |
|---|---|
| 5X Epimark ® HS Taq Reaction Buffer (New England Biolabs, Ipswich, MA) | 10 μl |
| 10 mM dNTPs | 1 μl |
| 10 μM Forward Primer | 1 μl |
| 10 μM Reverse Primer | 1 μl |
| Deaminated Oligonucleotide (1 μM) | 1 μl |
| Epimark HS Taq DNA Polymerase | 0.25 μl |
| Nuclease-free water | 35.75 |

TABLE 7

PCR cycling protocol

| Cycling Step | Temp | Time |
|---|---|---|
| Initial denaturation | 95° C. | 1 minute |
| Denaturation | 95° C. | 30 seconds |

TABLE 7-continued

PCR cycling protocol

| Cycling Step | Temp | Time |
|---|---|---|
| Annealing | 56° C. | 30 seconds |
| Extension | 68° C. | 20 seconds |
| Final extension | 68° C. | 5 minutes |
| Number of cycles | | 25 cycles |

TABLE 8

MseI digestion

| Reaction Component | 20 µl 1x |
|---|---|
| PCR product | 8 |
| Nuclease-free water | 9.7 |
| NEBuffer 4 | 2 |
| MseI 10 u/µl | 0.3 |

The reaction mixture was incubated at 37° C. for 0.5 hours and the DNA digestion products were analyzed on 2% agarose gel (see FIG. 7A-D). The 5-mC was converted to T and the PCR product formed after this conversion could be cleaved by the restriction endonuclease MseI.

B. APOBEC-3A Activity Assay on U$^{5m}$C Containing Substrate

1 µl of human APOBEC-3A from PURExpress system extract was serially diluted 1:1, 1:2, 1:4, 1:8, 1:16, 1:32, 1:64 and reacted with 1 pM ssDNA (TATGGGGAAGGT-TAGGGAAGATAAGAATAGAATGATUmCTAAGGAT-GAATATGAGGTGAGGAGTAGGATGGG (SEQ ID NO:17) in NEBuffer 1 (10 mM Bis-Tris-Propane-HCl, 10 mM MgCl$_2$ 1 mM Dithiothreitol pH 7.0) in the presence of RNaseA (1 µg). Reactions were incubated for 14 hours (overnight) at 37° C. Deaminations were detected through PCR reaction (FW primer: 5'-CCATCTCATCCCTGCGT-GTCTCCGACTCAGTATGGGGAAGGTTAGGGAAG (SEQ ID NO:18), REV primer: 5'-CCTCTCTATGGGCA-GTCGGTGATCCCATCCTACTCCTCACCTC (SEQ ID NO:19)) and digestion with MseI restriction endonuclease as described in Example 3 and shown in FIGS. 7C and 7D.

Example 4: APOBEC-3A Activity Assay on 5-hmC Containing Substrate

1 µl of APOBEC-3A from PURExpress extract was reacted with 1 pM fluorescein (F)-labeled ssDNA in NEBuffer 1 (10 mM Bis-Tris-Propane-HCl, 10 mM MgCl$_2$ 1 mM Dithiothreitol pH 7.0) in the presence of RNaseA (1 µg). Reactions were incubated for 60 minutes at 37° C. Deaminations were detected through breakage of DNA at abasic sites generated by 0.5 µl of each of SMUG1 (5 u/µl) and EndoVIII (10 u/µl) enzyme. The results are shown on a urea gel and show no conversion of 5-hmC to U except using when using the control oligonucleotide containing 5-hmU and SMUG1/EndoVIII which produces the second band. The results are shown in FIG. 8A-B in which none of the 5-hmC is observed to be converted to 5-hmU.

Example 5: APOBEC-3A Deaminates 5m-C but not 5-hmC in Bisulfite Converted DNA

A DNA substrate of 489 bp long containing four CpG sequences at positions 80, 174, 239 and 356 was methyl in vitro with SssI methylase (New England Biolabs, Ipswich, Mass.). Methyl substrate was bisulfite converted using EpiMark Bisulfite Conversion Kit, amplified using FW GAG-GAGGAAAAGAGAAATGGAGTGTGG (SEQ ID NO:20) and REV CTCACACCTCTCCTCTCACTCAC (SEQ ID NO:21) primers and EpiMark HS Taq DNA Polymerase. PCR fragment was inserted into TOPO TA Cloning vector and transformed into NEB 5-alpha F'/$^q$ Competent E. coli. When tested by sequencing, it was found that 100% of 5-mCs were identified as C.

Figure 12:
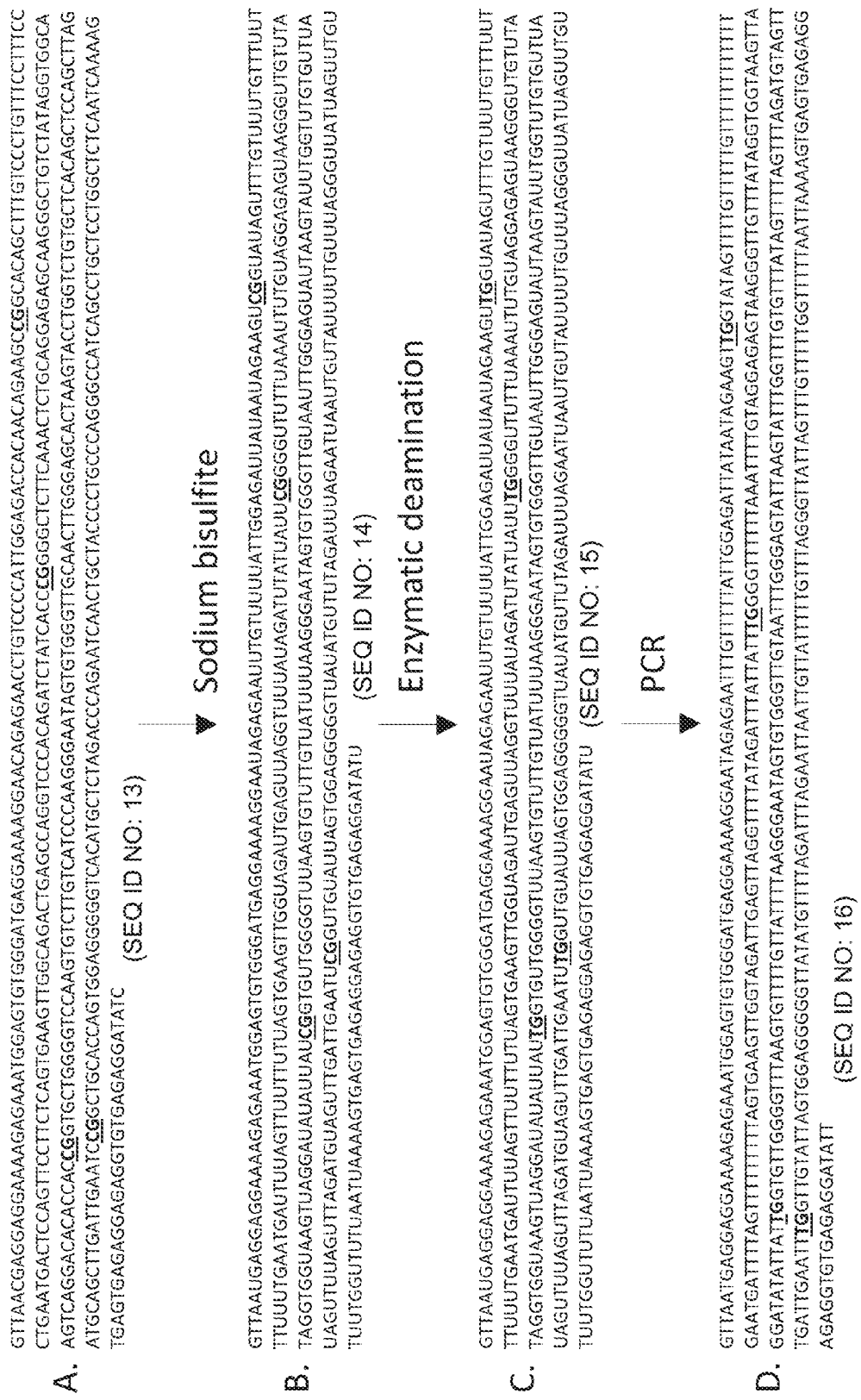

An aliquot of the bisulfite converted DNA sample was treated with cytidine deaminase, or a mixture of cytidine deaminases for 4 hours to convert all 5-mCs to Ts (described in Example 1). After the reaction was completed, the deaminated DNA was amplified using FW GAGGAG-GAAAAGAGAAATGGAGTGTGG (SEQ ID NO:20) and REV CTCACACCTCTCCTCTCACTCAC (SEQ ID NO:21) primers and Epimark HS Taq DNA Polymerase. PCR fragment was inserted into TOPO TA cloning vector and transformed into NEB 5-alpha F'/$^q$ Competent E. coli. When tested by sequencing, it was found that 100% of 5-mCs were identified as Ts. The results are shown in FIGS. 11 and 12.

Example 6: Discrimination Between 5-mC and 5-hmC Using Cytidine Deaminase and DNA Oxygenase Enzymes Bisulfite sequencing in Example 5 was replaced here by sequential oxygenase and deaminase treatment.

A. Use of TET as the Oxygenase

The oxygenase reaction was performed as follows: 100 ng of NIH 3T3 Mouse Genomic DNA (New England Biolabs, Ipswich, Mass.) was incubated with TET1 (WiseGene, Chicago, Ill.) in 50 µl of reaction mixture for 3 hours. DNA was cleaned up using Zymo Clean & Concentrator™ kit (Zymo Research, Irvine, Calif.).

TET is active on dsDNA. 50 µl of TET treated and untreated NIH 3T3 Mouse Genomic DNA in two separate tubes were heated up to 99° C. for 5 minutes, spun down briefly and put on ice.

B. Use of mYOX1 Instead of TET as the Oxygenase

In this example, a double-stranded substrate, containing 5-mC was oxidized with mYOX1. mYOX1 is active on ssDNA.

The sequence of the substrate was:

```
                                              (SEQ ID NO: 22)
CGGCGTTTCCGGGTTCCATAGGCTCCGCCCXGGACTCTGATGACCA
GGGCATCACA
(X = 5 - mC)
```

TABLE 9

Reaction components for reaction of oligonucleotide with mYOX1

| Reaction Component | Volume, µl | Stock | Final Concentration |
|---|---|---|---|
| ddH$_2$O | 3 | | to 20 µL |
| Bis-Tris pH 6.0 | 1 | 1M | 50 mM |
| NaCl | 1 | 1M | 5 0 mM |
| DTT | 1 | 20 mM | 1 mM |
| Ascorbic acid | 2 | 20 mM | 2 mM |
| α-ketoglutarate | 2 | 10 mM | 1 mM |
| FeSO$_4$ | 1 | 2 mM | 100 µM |
| Oligonucleotide | 4 | 10 µM | 2 µM |
| MYOX1 | 5 | 16 µM | 4 µM |

The sequence for mYOX1 is as follows:

(SEQ ID NO: 23)
MTTFKQQTIKEKETKRKYCIKGTTANLTQTHPNGPVCVNRGEEVAN

TTTLLDSGGGINKKSLLQNLLSKCKTTFQQSFTNANITLKDEKWLK

NVRTAYFVCDHDGSVELAYLPNVLPKELVEEFTEKFESIQTGRKKD

TGYSGILDNSMPFNYVTADLSQELGQYLSEIVNPQINYYISKLLTC

VSSRTINYLVSLNDSYYALNNCLYPSTAFNSLKPSNDGHRIRKPHK

DNLDITPSSLFYFGNFQNTEGYLELTDKNCKVFVQPGDVLFFKGNE

YKHVVANITSGWRIGLVYFAHKGSKTKPYYEDTQKNSLKIHKETK

The reaction mixture was incubated at 34° C. for 1 hour. 1 μL of Proteinase K (20 mg/mL$^{-1}$) (New England Biolabs, Ipswich, Mass.) was added to the reaction mixture and incubated for 1 hour at 50° C. DNA was isolated using the QIAquick® Nucleotide Removal Kit (Qiagen, Germany) and samples were analyzed by LC/MS.

These conditions cause 5-mC to be oxidized to 5-hmC. Oxidation with mYOX1 of Mouse NIH 3T3 Genomic DNA

TABLE 10

Reaction components for oxygenase treatment of genomic DNA

| Reaction Component | Volume, μl | Stock | Final Concentration |
|---|---|---|---|
| ddH$_2$O | 15 | | to 50 μl |
| Bis-Tris pH 6.0 | 2.5 | 1M | 50 mM |
| NaCl | 2.5 | 1M | 50 mM |
| DTT | 2.5 | 20 mM | 1 mM |
| Ascorbic acid | 5 | 20 mM | 2 mM |
| α-ketoglutarate | 5 | 10 mM | 1 mM |
| FeSO$_4$ | 2.5 | 2 mM | 100 μM |

TABLE 10-continued

Reaction components for oxygenase treatment of genomic DNA

| Reaction Component | Volume, μl | Stock | Final Concentration |
|---|---|---|---|
| NIH 3T3 DNA | 10 | 200 ng/μL | 2 μg |
| mYOX1 | 5 | 200 μM | 20 μM |

Human APOBEC-3A (100 ng from example 1), RNaseA (1 μg) were combined with ssDNA substrate (oxidated and non-oxidated NIH 3T3 Mouse Genomic DNA in separate tubes) and incubated in the reaction buffer (NEBuffer 1, (10 mM Bis-Tris-Propane-HCl, 10 mM MgCl2 1 mM Dithiothreitol pH 7.0)) at 37° C. for 12-16 hours. Reactions were terminated by incubating at 80° C. for 10 minutes.

The oxidized and deaminated DNA or deaminated DNA only were PCR amplified and cloned. 2 μl from each sample (TET1+Deaminase and Deaminase only) were used for the PCR reaction using Epimark HS Taq DNA Polymerase. Primers were designed for deaminated DNA (all Cs become Ts, except oxidized 5m-C or 5hm-C). PCR products were visualized on 1.5% agarose gel and cloned into the TOPO TA Cloning vector and transformed into NEB 5-alpha F'/$^q$ Competent E. coli. DNA was isolated from individual colonies and sequenced using nested primers.

The sequence results were interpreted as follows:
(a) Original sequence: GGGTmCGGACCGhmC (SEQ ID NO:7)
(b) After TET and deaminase treatment:GGGTCGGATTGC (SEQ ID NO:11)
(c) After deaminase only treatment: GGGTTGGATTGC (SEQ ID NO:12)

After alignment of sequences, TET and deaminase treatment (b) and deaminase only treatment (c) show Cs that corresponds to 5-hmC but not C. After TET and deaminase treatment only, C also corresponds to 5-mC but after deaminase treatment only, 5-mC corresponds to T.

What is claimed is:

1. A composition comprising a protein variant having at least 90% sequence identity to:
   (a) SEQ ID NO:1 and comprising an Asp at the position corresponding to position 180 in SEQ ID NO:1 and:
      i. an amino acid that is not Ser at the position corresponding to position 45 in SEQ ID NO:1,
      ii. an amino acid that is not Glu at the position corresponding to position 109 in SEQ ID NO:1, and
      iii. an amino acid that is not Arg at the position corresponding to position 123 in SEQ ID NO:1;
   (b) SEQ ID NO:2 and comprising an Arg at the position corresponding to position 29 in SEQ ID NO:2, an Arg at the position corresponding to position 104 in SEQ ID NO:2, an Arg at the position corresponding to position 123 in SEQ ID NO:2 and:
      i. an amino acid that is not a Thr at the position corresponding to position 23 in SEQ ID NO:2,
      ii. an amino acid that is not Gly at the position corresponding to position 25 in SEQ ID NO:2, and
      iii. an amino acid that is not Cys at the position corresponding to position 69 in SEQ ID NO:2, or
   (c) SEQ ID NO:3 (activation induced cytidine deaminase (AID)) and comprising a deletion at a position corresponding to position 117 of SEQ ID NO: 3.

2. A composition according to claim 1, further comprising at least one of a purified oxygenase, a polymerase, a polynucleotide and/or at least one primer and dNTPs.

3. An in vitro mixture comprising a protein variant of claim 1 and a purified oxygenase.

4. An in vitro mixture according to claim 3, wherein the oxygenase is a methyl pyrimidine oxygenase or a 5-methylcytosine oxygenase.

5. An in vitro mixture according to claim 3, wherein the protein variant has at least 90% sequence identity to:
   (a) SEQ ID NO:1 and comprises an Asp at the position corresponding to position 180 in SEQ ID NO:1 and:
      i. a Trp at the position corresponding to position 45 in SEQ ID NO:1,
      ii. a Gln at the position corresponding to position 109 in SEQ ID NO:1, and
      iii. aft His at the position corresponding to position 123 in SEQ ID NO:1, or
   (b) SEQ ID NO:2 and comprises an Arg at the position corresponding to position 29 in SEQ ID NO:2, an Arg at the position corresponding to position 104 in SEQ ID NO:2, an Arg at the position corresponding to position 123 in SEQ ID NO:2 and:
      i. an Asn at the position corresponding to position 23 in SEQ ID NO:2,
      ii. a Val at the position corresponding to position 25 in SEQ ID NO:2, and
      iii. an Arg at the position corresponding to position 69 in SEQ ID NO:2.

6. An in vitro mixture according to claim 4, wherein the methyl pyrimidine oxygenase is mYOX.

7. An in vitro mixture according to claim 4, wherein the 5-methylcytosine oxygenase is TET1.

8. An in vitro mixture, comprising a purified cytidine deaminase and a purified DNA polymerase, wherein the purified cytidine deaminase has at least 90% sequence identity to:
   (a) SEQ ID NO:1 and comprises an Asp at the position corresponding to position 180 in SEQ ID NO:1 and:
      i. an amino acid that is not Ser at the position corresponding to position 45 in SEQ ID NO:1,
      ii. an amino acid that is not Glu at the position corresponding to position 109 in SEQ ID NO:1, and
      iii. an amino acid that is not Arg at the position corresponding to position 123 in SEQ ID NO:1,
   (b) SEQ ID NO:2 and comprises an Arg at the position corresponding to position 29 in SEQ ID NO:2, an Arg at the position corresponding to position 104 in SEQ ID NO:2, an Arg at the position corresponding to position 123 in SEQ ID NO:2 and:
      i. an amino acid that is not Thr at the position corresponding to position 23 in SEQ ID NO:2,
      ii. an amino acid that is not Gly at the position corresponding to position 25 in SEQ ID NO:2, and
      iii. an amino acid that is not Cys at the position corresponding to position 69 in SEQ ID NO:2, or
   (c) SEQ ID NO:3 and comprises a deletion at a position corresponding to position 117 of SEQ ID NO: 3.

9. An in vitro mixture according to claim 8, further comprising a polynucleotide and at least one primer and dNTPs.

10. A method for determining for a cytidine deaminase, a cytosine preference according to an adjacent nucleotide, comprising:
    (a) reacting a polynucleotide containing a cytosine with a protein variant of claim 1 to convert the cytosine to uracil where the cytosine may be adjacent to any of adenine, guanine, thymine, uracil or cytosine;
    (b) reacting the product of (a) with a glycosylase and an AP endonuclease so as to cleave the polynucleotide at the uracil;
    (c) detecting the cleavage product from (b) to determine the activity of the cytidine deaminase for the cytosine adjacent to any of adenine, guanine, thymine, uracil or cytosine.

11. A method according to claim 10, wherein the polynucleotide is single stranded.

12. A method according to claim 11, wherein the polynucleotide is labeled at one end.

13. The composition of claim 1, wherein the protein has at least 90% sequence identity to SEQ ID NO:1, an Asp at the position corresponding to position 180 in SEQ ID NO:1 and:
    i. an amino acid that is not Ser at the position corresponding to position 45 in SEQ ID NO:1,
    ii. an amino acid that is not Glu at the position corresponding to position 109 in SEQ ID NO:1, and iii. an amino acid that is not Arg at the position corresponding to position 123 in SEQ ID NO:1.

14. The composition of claim 1, wherein the protein has at least 90% sequence identity to SEQ ID NO:2 and comprises an Arg at the position corresponding to position 29 in SEQ ID NO:2, an Arg at the position corresponding to position 104 in SEQ ID NO:2, an Arg at the position corresponding to position 123 in SEQ ID NO:2 and:
  i. an amino acid that is not Thr at the position corresponding to position 23 in SEQ ID NO:2,
  ii. an amino acid that is not Gly at the position corresponding to position 25 in SEQ ID NO:2, and
  iii. an amino acid that is not Cys at the position corresponding to position 69 in SEQ ID NO:2.

15. The composition of claim 1, wherein the protein has at least 90% sequence identity to SEQ ID NO:3 and comprises a deletion at a position corresponding to position 117 of SEQ ID NO: 3.

* * * * *